(12) United States Patent
Balda

(10) Patent No.: US 9,226,679 B2
(45) Date of Patent: *Jan. 5, 2016

(54) SYSTEMS AND METHODS FOR INTERELECTRODE DISTANCE OPTIMIZATION IN A RETRACTABLE MULTI-USE CARDIAC MONITOR

(71) Applicant: Medicomp, Inc, Melbourne, FL (US)

(72) Inventor: Daniel Balda, Indian Harbour Beach, FL (US)

(73) Assignee: Medicomp, Inc., Melbourne, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/616,801

(22) Filed: Feb. 9, 2015

(65) Prior Publication Data

US 2015/0150471 A1   Jun. 4, 2015

Related U.S. Application Data

(63) Continuation of application No. 13/111,517, filed on May 19, 2011, now Pat. No. 8,989,850.

(60) Provisional application No. 61/347,117, filed on May 21, 2010.

(51) Int. Cl.
*A61B 5/0408* (2006.01)
*A61B 5/00* (2006.01)
(Continued)

(52) U.S. Cl.
CPC .............. *A61B 5/0408* (2013.01); *A61B 5/0006* (2013.01); *A61B 5/0404* (2013.01);
(Continued)

(58) Field of Classification Search
CPC .. A61B 5/0404; A61B 5/0408; A61B 5/0006; A61B 5/6823; A61B 5/6826; A61B 2560/045; A61B 2562/221; A61B 5/044; A61B 5/045
USPC .................. 600/382, 386, 391–392, 509, 523
See application file for complete search history.

(56) References Cited

U.S. PATENT DOCUMENTS 4,606,352 A  *  8/1986  Geddes et al. ................ 600/515
4,622,979 A      11/1986  Katchis et al.
(Continued)

FOREIGN PATENT DOCUMENTS

CN   101278833 A   10/2008
EP   2664273 A1   11/2013
(Continued)

OTHER PUBLICATIONS

Puurtinen et al., "Estimation of ECG signal of closely separated bipolar electrodes using thorax models," Proceedings of the 26th Annual International Conference of the IEEE EMBS, San Francisco, California, Sep. 1-5, 2004, 801-804.
(Continued)

*Primary Examiner* — Mark W Bockelman
(74) *Attorney, Agent, or Firm* — Mark Malek; William Harding; Widerman Malek, PL

(57) ABSTRACT

A retractable multi-use cardiac monitor is provided that includes a memory, and first and second sensing connectors positioned on outsides of first and second housings, respectively. The first and second sensing connectors are configured to detect electrocardiogram (ECG) signals that are stored onto the memory as ECG data. The second housing of the retractable multi-use cardiac monitor also includes a wire retractor configured to extend and retract a wire that connects the second and first housings, and that defines an interelectrode distance between the first and second sensing connectors. The retractable multi-use cardiac monitor further includes systems and methods for determining a length for the interelectrode distance that is optimum in terms of strength and fidelity of the detected ECG signals. The retractable multi-use cardiac monitor further includes a wireless radio configured to transmit a portion of the stored ECG data from the memory to a destination.

20 Claims, 11 Drawing Sheets

(51) Int. Cl.
*A61B 5/0404* (2006.01)
*A61B 5/0432* (2006.01)
*A61B 5/044* (2006.01)

(52) U.S. Cl.
CPC ............ *A61B 5/044* (2013.01); *A61B 5/04325* (2013.01); *A61B 5/6823* (2013.01); *A61B 5/6826* (2013.01); *A61B 2560/045* (2013.01); *A61B 2562/221* (2013.01)

(56) References Cited

U.S. PATENT DOCUMENTS

| | | | |
|---|---|---|---|
| 4,858,617 A * | 8/1989 | Sanders | 600/509 |
| 4,938,228 A | 7/1990 | Righter et al. | |
| 4,947,846 A | 8/1990 | Kitagawa et al. | |
| 5,307,818 A | 5/1994 | Segalowitz | |
| 5,398,183 A | 3/1995 | Elliott | |
| 5,730,143 A | 3/1998 | Schwarzberg | |
| 5,813,979 A * | 9/1998 | Wolfer | 600/373 |
| 5,931,791 A | 8/1999 | Saltzstein et al. | |
| 5,941,829 A | 8/1999 | Saltzstein et al. | |
| 5,959,529 A | 9/1999 | Kail | |
| 6,117,077 A | 9/2000 | Del Mar et al. | |
| 6,225,901 B1 | 5/2001 | Kail | |
| 6,287,252 B1 | 9/2001 | Lugo | |
| 6,456,872 B1 | 9/2002 | Faisandier | |
| 6,496,715 B1 | 12/2002 | Lee et al. | |
| 6,546,285 B1 | 4/2003 | Owen et al. | |
| 6,567,680 B2 | 5/2003 | Swetlik et al. | |
| 6,569,095 B2 | 5/2003 | Eggers | |
| 6,605,046 B1 | 8/2003 | Del Mar | |
| 6,664,893 B1 | 12/2003 | Eveland et al. | |
| 6,665,385 B2 | 12/2003 | Rogers et al. | |
| 6,690,959 B2 | 2/2004 | Thompson | |
| 6,694,177 B2 | 2/2004 | Eggers et al. | |
| 6,801,137 B2 | 10/2004 | Eggers | |
| 6,871,089 B2 | 3/2005 | Korzinov et al. | |
| 6,897,788 B2 | 5/2005 | Khair et al. | |
| 6,940,403 B2 | 9/2005 | Kail | |
| 6,957,107 B2 | 10/2005 | Rogers et al. | |
| 6,987,965 B2 | 1/2006 | Ng et al. | |
| 7,002,468 B2 | 2/2006 | Eveland et al. | |
| 7,092,750 B2 | 8/2006 | Van Ess | |
| 7,099,715 B2 | 8/2006 | Korzinov et al. | |
| 7,130,396 B2 | 10/2006 | Rogers et al. | |
| 7,194,300 B2 | 3/2007 | Korzinov | |
| 7,206,630 B1 | 4/2007 | Tarler | |
| 7,212,850 B2 | 5/2007 | Prystowsky et al. | |
| 7,257,438 B2 | 8/2007 | Kinast | |
| 7,286,865 B2 | 10/2007 | Nazeri | |
| 7,299,085 B2 | 11/2007 | Bergelson et al. | |
| 7,444,177 B2 | 10/2008 | Nazeri | |
| 7,554,828 B2 | 6/2009 | Wilson | |
| 7,587,237 B2 | 9/2009 | Korzinov et al. | |
| 7,668,588 B2 | 2/2010 | Kovacs | |
| 7,729,753 B2 | 6/2010 | Kremliovsky et al. | |
| 7,764,988 B2 | 7/2010 | Drew et al. | |
| D621,048 S | 8/2010 | Severe et al. | |
| 7,787,943 B2 | 8/2010 | McDonough | |
| D634,431 S | 3/2011 | Severe et al. | |
| 7,907,996 B2 | 3/2011 | Prystowsky et al. | |
| 7,941,207 B2 | 5/2011 | Korzinov | |
| 7,970,450 B2 | 6/2011 | Kroecker et al. | |
| 7,996,075 B2 | 8/2011 | Korzinov et al. | |
| 8,016,776 B2 | 9/2011 | Bourget et al. | |
| 8,108,033 B2 | 1/2012 | Drew et al. | |
| 8,116,841 B2 | 2/2012 | Bly et al. | |
| 8,160,682 B2 | 4/2012 | Kumar et al. | |
| 8,160,703 B2 | 4/2012 | Stickney et al. | |
| D659,836 S | 5/2012 | Bensch et al. | |
| 8,200,319 B2 | 6/2012 | Pu et al. | |
| 8,214,007 B2 | 7/2012 | Baker et al. | |
| 8,239,012 B2 | 8/2012 | Felix et al. | |
| 8,249,686 B2 | 8/2012 | Libbus et al. | |
| 8,255,046 B2 | 8/2012 | Sarkar et al. | |
| 8,273,053 B2 | 9/2012 | Saltzstein | |
| RE43,767 E | 10/2012 | Eggers et al. | |
| 8,285,356 B2 | 10/2012 | Bly et al. | |
| 8,285,370 B2 | 10/2012 | Felix et al. | |
| 8,290,129 B2 | 10/2012 | Rogers et al. | |
| 8,315,687 B2 | 11/2012 | Cross et al. | |
| 8,374,688 B2 | 2/2013 | Libbus et al. | |
| 8,425,414 B2 | 4/2013 | Eveland | |
| 8,444,578 B2 | 5/2013 | Bourget et al. | |
| 8,449,469 B2 | 5/2013 | Banet et al. | |
| 8,449,471 B2 | 5/2013 | Tran | |
| 8,460,189 B2 | 6/2013 | Libbus et al. | |
| 8,473,039 B2 | 6/2013 | Michelson et al. | |
| 8,483,809 B2 | 7/2013 | Kim et al. | |
| 8,506,480 B2 | 8/2013 | Banet et al. | |
| 8,515,529 B2 | 8/2013 | Pu et al. | |
| 8,538,503 B2 | 9/2013 | Kumar et al. | |
| 8,550,997 B2 | 10/2013 | Talbot et al. | |
| 8,560,040 B2 | 10/2013 | Gehman et al. | |
| 8,560,046 B2 | 10/2013 | Kumar et al. | |
| 8,565,864 B2 | 10/2013 | Drew et al. | |
| 8,611,980 B2 | 12/2013 | Choe et al. | |
| 8,613,708 B2 | 12/2013 | Bishay et al. | |
| 8,613,709 B2 | 12/2013 | Bishay et al. | |
| 8,620,402 B2 | 12/2013 | Parker et al. | |
| 8,626,262 B2 | 1/2014 | McGusty et al. | |
| 8,630,699 B2 | 1/2014 | Baker et al. | |
| 8,639,319 B2 | 1/2014 | Hugh et al. | |
| 8,663,106 B2 | 3/2014 | Stivoric et al. | |
| 8,688,189 B2 | 4/2014 | Shennib | |
| 8,688,190 B2 | 4/2014 | Libbus et al. | |
| 8,718,752 B2 | 5/2014 | Libbus et al. | |
| 8,734,339 B2 | 5/2014 | Rao et al. | |
| 8,744,562 B2 | 6/2014 | Giftakis et al. | |
| 8,773,258 B2 | 7/2014 | Vosch et al. | |
| 8,782,308 B2 | 7/2014 | Vlach | |
| 8,790,257 B2 | 7/2014 | Libbus et al. | |
| 8,795,174 B2 | 8/2014 | Manicka et al. | |
| 8,798,728 B2 | 8/2014 | Drew et al. | |
| 8,814,792 B2 | 8/2014 | Raptis et al. | |
| 8,818,481 B2 | 8/2014 | Bly et al. | |
| 8,823,490 B2 | 9/2014 | Libbus et al. | |
| 8,838,218 B2 | 9/2014 | Khair | |
| 8,897,868 B2 | 11/2014 | Mazar et al. | |
| 8,909,832 B2 | 12/2014 | Vlach et al. | |
| 8,945,019 B2 | 2/2015 | Prystowsky et al. | |
| 8,965,492 B2 | 2/2015 | Baker et al. | |
| 8,965,498 B2 | 2/2015 | Katra et al. | |
| 8,989,850 B2 * | 3/2015 | Balda | 600/509 |
| 9,017,255 B2 | 4/2015 | Raptis et al. | |
| 9,021,161 B2 | 4/2015 | Vlach et al. | |
| 9,044,148 B2 | 6/2015 | Michelson et al. | |
| 2002/0045836 A1 | 4/2002 | Alkawwas | |
| 2002/0067256 A1 | 6/2002 | Kail | |
| 2004/0006265 A1 | 1/2004 | Alhussiny | |
| 2004/0077954 A1 * | 4/2004 | Oakley et al. | 600/483 |
| 2004/0260189 A1 | 12/2004 | Eggers et al. | |
| 2005/0049515 A1 * | 3/2005 | Misczynski et al. | 600/509 |
| 2005/0113661 A1 | 5/2005 | Nazeri et al. | |
| 2005/0119580 A1 | 6/2005 | Eveland | |
| 2006/0030781 A1 | 2/2006 | Shennib | |
| 2006/0030782 A1 | 2/2006 | Shennib | |
| 2006/0069320 A1 | 3/2006 | Wolff et al. | |
| 2006/0095091 A1 | 5/2006 | Drew | |
| 2006/0276715 A1 | 12/2006 | Yeo et al. | |
| 2007/0129769 A1 | 6/2007 | Bourget et al. | |
| 2007/0149887 A1 | 6/2007 | Hwang et al. | |
| 2007/0156054 A1 | 7/2007 | Korzinov et al. | |
| 2007/0293776 A1 | 12/2007 | Korzinov et al. | |
| 2008/0097231 A1 * | 4/2008 | Balda et al. | 600/509 |
| 2008/0108890 A1 | 5/2008 | Teng et al. | |
| 2008/0177168 A1 | 7/2008 | Callahan et al. | |
| 2008/0275327 A1 | 11/2008 | Faarbaek et al. | |
| 2009/0062670 A1 | 3/2009 | Sterling et al. | |
| 2009/0076342 A1 | 3/2009 | Amurthur et al. | |
| 2010/0056881 A1 | 3/2010 | Libbus et al. | |
| 2010/0168578 A1 | 7/2010 | Garson et al. | |
| 2010/0249541 A1 | 9/2010 | Geva et al. | |
| 2010/0249624 A1 | 9/2010 | Peng | |

(56) References Cited

U.S. PATENT DOCUMENTS

| | | |
|---|---|---|
| 2010/0249625 A1 | 9/2010 | Lin |
| 2010/0268103 A1 | 10/2010 | McNamara et al. |
| 2010/0317958 A1 | 12/2010 | Beck et al. |
| 2011/0144470 A1 | 6/2011 | Mazar et al. |
| 2011/0160601 A1 | 6/2011 | Wang et al. |
| 2011/0166464 A1 | 7/2011 | Lee et al. |
| 2011/0218418 A1 | 9/2011 | Green et al. |
| 2011/0270100 A1* | 11/2011 | Chang ............ 600/509 |
| 2012/0029313 A1 | 2/2012 | Burdett et al. |
| 2012/0089001 A1 | 4/2012 | Bishay et al. |
| 2012/0101396 A1 | 4/2012 | Solosko et al. |
| 2012/0197150 A1 | 8/2012 | Cao et al. |
| 2012/0330126 A1 | 12/2012 | Hoppe et al. |
| 2013/0030259 A1 | 1/2013 | Thomsen et al. |
| 2013/0060098 A1 | 3/2013 | Thomsen et al. |
| 2013/0109937 A1 | 5/2013 | Banet et al. |
| 2013/0116520 A1 | 5/2013 | Roham et al. |
| 2013/0116533 A1 | 5/2013 | Lian et al. |
| 2013/0116585 A1 | 5/2013 | Bouguerra |
| 2013/0150698 A1 | 6/2013 | Hsu et al. |
| 2013/0204100 A1 | 8/2013 | Acquista |
| 2013/0225967 A1 | 8/2013 | Esposito |
| 2013/0226018 A1 | 8/2013 | Kumar et al. |
| 2013/0231577 A1 | 9/2013 | Leiderman |
| 2013/0245415 A1 | 9/2013 | Kumar et al. |
| 2013/0274584 A1 | 10/2013 | Finlay et al. |
| 2013/0289424 A1 | 10/2013 | Brockway et al. |
| 2013/0296667 A1 | 11/2013 | Rastegar et al. |
| 2013/0331678 A1 | 12/2013 | Lading et al. |
| 2013/0338448 A1 | 12/2013 | Libbus et al. |
| 2014/0094676 A1 | 4/2014 | Gani et al. |
| 2014/0100432 A1 | 4/2014 | Golda et al. |
| 2014/0128712 A1 | 5/2014 | Banet et al. |
| 2014/0128713 A1 | 5/2014 | Banet et al. |
| 2014/0128714 A1 | 5/2014 | Banet et al. |
| 2014/0128757 A1 | 5/2014 | Banet et al. |
| 2014/0206976 A1 | 7/2014 | Thompson et al. |
| 2014/0206977 A1 | 7/2014 | Bahney et al. |
| 2014/0213879 A1 | 7/2014 | Choe et al. |
| 2014/0221772 A1 | 8/2014 | Wolloch et al. |
| 2014/0236249 A1 | 8/2014 | Rao et al. |
| 2014/0249443 A1 | 9/2014 | Banet et al. |
| 2014/0275932 A1 | 9/2014 | Zadig |
| 2014/0288385 A1 | 9/2014 | Amurthur et al. |
| 2014/0330088 A1 | 11/2014 | Libbus et al. |
| 2014/0350362 A1 | 11/2014 | Raptis et al. |
| 2014/0371604 A1 | 12/2014 | Katra et al. |
| 2014/0378799 A1 | 12/2014 | Chattaraj et al. |
| 2015/0005588 A1 | 1/2015 | Herken et al. |
| 2015/0005589 A1 | 1/2015 | Bly et al. |
| 2015/0005590 A1 | 1/2015 | Libbus et al. |
| 2015/0018657 A1 | 1/2015 | Bibian et al. |
| 2015/0022372 A1 | 1/2015 | Vosch |
| 2015/0057512 A1 | 2/2015 | Kapoor |
| 2015/0073252 A1 | 3/2015 | Mazar |
| 2015/0087921 A1 | 3/2015 | Felix et al. |
| 2015/0087922 A1 | 3/2015 | Bardy et al. |
| 2015/0087923 A1 | 3/2015 | Bardy et al. |
| 2015/0087949 A1 | 3/2015 | Felix et al. |
| 2015/0087950 A1 | 3/2015 | Felix et al. |
| 2015/0087951 A1 | 3/2015 | Felix et al. |
| 2015/0094552 A1 | 4/2015 | Golda et al. |
| 2015/0094556 A1 | 4/2015 | Geva et al. |
| 2015/0094557 A1 | 4/2015 | Hsu et al. |
| 2015/0094558 A1 | 4/2015 | Russell |
| 2015/0094559 A1 | 4/2015 | Russell |
| 2015/0094605 A1 | 4/2015 | Sabesan et al. |
| 2015/0105631 A1 | 4/2015 | Tran et al. |
| 2015/0105647 A1 | 4/2015 | Katra et al. |
| 2015/0126822 A1 | 5/2015 | Chavan et al. |
| 2015/0126848 A1 | 5/2015 | Baker et al. |
| 2015/0148622 A1 | 5/2015 | Moyer et al. |
| 2015/0148637 A1 | 5/2015 | Golda et al. |
| 2015/0148691 A1 | 5/2015 | Moyer et al. |
| 2015/0150505 A1 | 6/2015 | Kaskoun et al. |
| 2015/0150506 A1 | 6/2015 | Woo |

FOREIGN PATENT DOCUMENTS

| | | |
|---|---|---|
| GB | 2458389 A | 9/2009 |
| KR | 20140050374 A | 4/2014 |
| KR | 20140088390 A | 7/2014 |
| WO | WO2007094729 A1 | 8/2007 |
| WO | WO2008005016 A1 | 1/2008 |
| WO | WO20111467089 A2 | 11/2011 |
| WO | WO2014116816 A1 | 7/2014 |

OTHER PUBLICATIONS

International Search Report dated Jan. 19, 2012, cited in corresponding Patent Application No. PCT/US2011/037139, filed May 19, 2011 (4 pages).

Written Opinion dated Jan. 19, 2012, cited in corresponding Patent Application No. PCT/US2011/037139, filed May 19, 2011 (8 pages).

\* cited by examiner

SYSTEMS AND METHODS FOR INTERELECTRODE DISTANCE OPTIMIZATION IN A RETRACTABLE MULTI-USE CARDIAC MONITOR

RELATED APPLICATIONS

This application is a continuation and claims the benefit under 35 U.S.C. §120 of U.S. patent application Ser. No. 13/111,517 filed on May 19, 2011 and titled Retractable Multi-Use Cardiac Monitor, which in turn, claimed the benefit under 35 U.S.C. §119(e) of U.S. Provisional Patent Application No. 61/347,117, filed on May 21, 2010 and titled Retractable Multi-Use Cardiac Monitor, the entire contents of each of which are incorporated herein by reference to the extent that they do not conflict with the disclosure herein.

FIELD OF THE INVENTION

The present invention relates generally to the field of cardiac monitoring. Specifically, the present invention is directed towards a retractable multi-use cardiac monitor.

BACKGROUND

Cardiac monitoring systems are generally comprised of a series of electrodes attached to the chest area of a patient to collect electrocardiogram (ECG) data. The series of electrodes are usually connected to a series of wires. However, the inventor has perceived that the series of electrodes and interconnected wires are not provided in a compact portable form that allows for easy adjustment of the vector length between the electrodes.

Accordingly, the inventor has perceived that there is a need for a retractable multi-use cardiac monitor that is compact in form and allows for easy adjustment of the vector length between the electrodes of the retractable multi-use cardiac monitor.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention provide a retractable multi-use cardiac monitor that advantageously allows for easy and function-enhancing adjustment of the vector length between the electrodes of the retractable multi-use cardiac monitor.

According to one embodiment, the retractable multi-use cardiac monitor includes a processor and a memory, a first side comprising a first housing wherein a first sensing connector is on the outside of the first housing, and wherein the first sensing connector is configured to collect electrocardiogram (ECG) data and store ECG data onto the memory. The retractable multi-use cardiac monitor further includes a second side comprising a second housing including a wire retractor and a second sensing connector, wherein the second sensing connector is on the outside of the second housing, and the wire retractor is configured to extend and retract a wire that connects the second and first sides, and wherein the second sensing connector is configured to collect ECG data and store ECG data onto the memory, and a wireless radio configured to transmit a portion of collected ECG data from the memory to a destination.

According to another embodiment, a method of collecting electrocardiogram (ECG) data with a retractable multi-use cardiac monitor is provided, wherein the retractable multi-use cardiac monitor includes a processor and a memory, a first side that includes a first housing wherein a first sensing connector is on the outside of the first housing, a second side including a second housing and a second sensing connector, wherein the second sensing connector is on the outside of the second housing, and a wireless radio. The method includes collecting ECG data from the first and second sensing connectors of the retractable multi-use cardiac monitor, wherein the first and second sensing connectors are placed against the skin of a chest area of a human patient, recording the collected ECG data onto the memory of the retractable multi-use cardiac monitor, and transmitting a portion of the collected ECG data to a destination.

According to yet another embodiment, a method of determining an optimum electrode vector length between a first sensing connector of a first side of a retractable multi-use cardiac monitor and a second sensing connector of a second side of the retractable multi-use cardiac monitor is provided. The method includes (A) receiving from the retractable multi-use cardiac monitor at a smart phone data representing a distance between the first sensing connector of the retractable multi-use cardiac data monitor and the second sensing connector of the retractable multi-use cardiac data monitor, wherein the smart phone includes a processor, (B) receiving electrocardiogram (ECG) data collected by the retractable multi-use cardiac data monitor through the first and second sensing connectors, (C) recording the ECG data collected in step B and the data representing the distance between the first and second sensing connectors received in step A, and (D) iteratively repeating steps A-C a number of times. The method further includes (E) calculating, by the processor of the smart phone, an optimum electrode vector length between the first sensing connector of the first side of the retractable multi-use cardiac monitor and the second sensing connector of the second side of the retractable multi-use cardiac monitor based on the ECG data collected in step B and the data representing the distance between the first and second sensing connectors received in step A, and (F) generating a notification of that the optimum electrode vector length has been found.

According to yet another embodiment a method of determining an optimum electrode vector length between a first sensing connector of a first side of a retractable multi-use cardiac monitor and a second sensing connector of a second side of the retractable multi-use cardiac monitor is provided. The method includes (A) determining a distance between the first sensing connector of the retractable multi-use cardiac data monitor and the second sensing connector of the retractable multi-use cardiac data monitor, and recording data representing the distance, (B) collecting electrocardiogram (ECG) data through the first and second sensing connectors and recording the collected ECG data, and (C) iteratively repeating A-B a number of times. The method further includes (E) calculating, by a processor of the retractable multi-use cardiac monitor, an optimum electrode vector length between the first sensing connector of the first side of the retractable multi-use cardiac monitor and the second sensing connector of the second side of the retractable multi-use cardiac monitor based on the ECG data collected in step B and the data representing the distance between the first and second sensing connectors recorded in step A, and (F) generating a notification of that the optimum electrode vector length has been found.

DETAILED DESCRIPTION OF THE INVENTION

Figure 1:
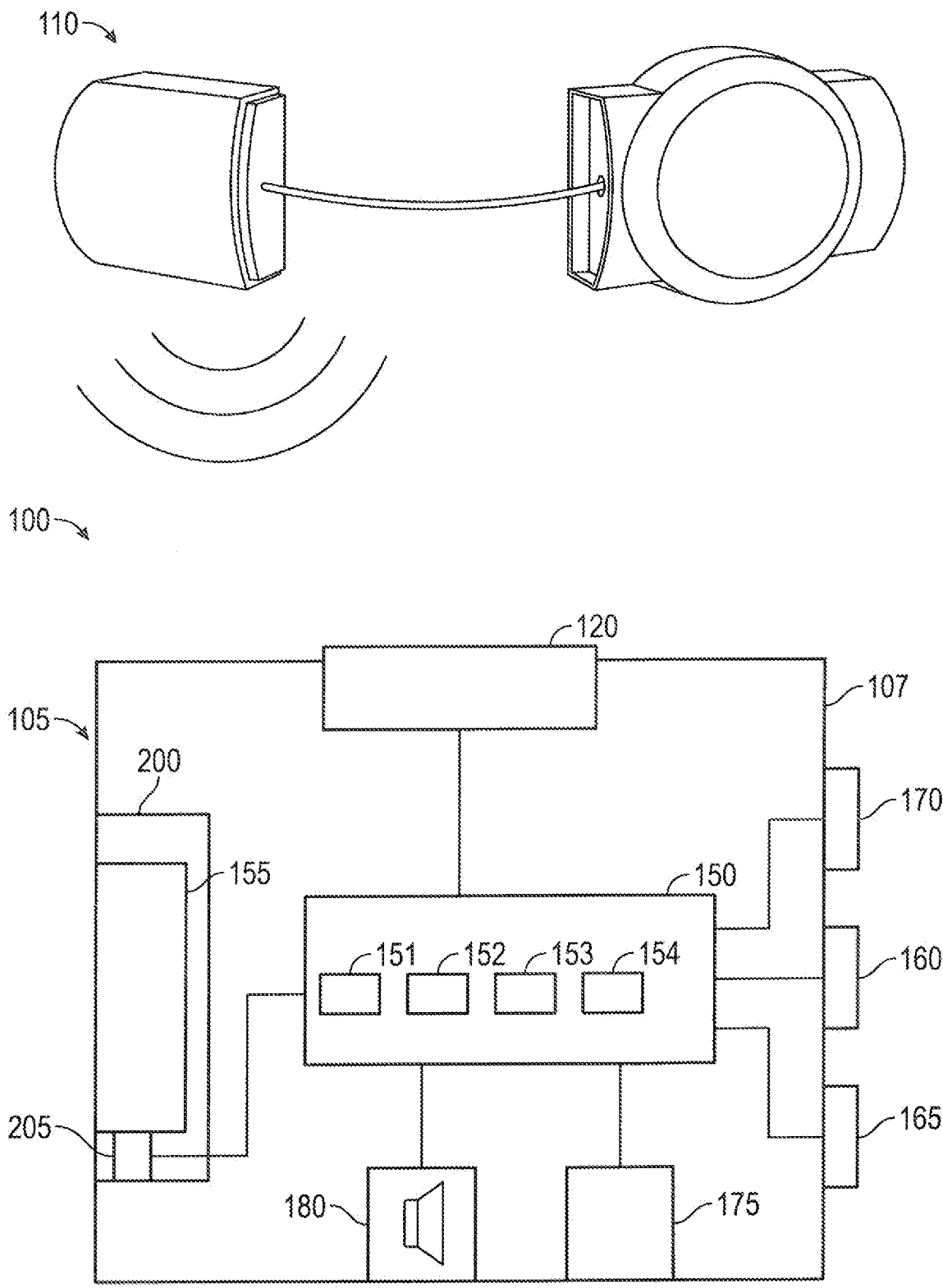
FIG. 1 is an illustration of a cardiac monitor system, according to one embodiment.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item. With regard to the present disclosure, terms such as "left", "right", and "portion" are used to identify parts of the disclosed retractable multi-use cardiac monitor and are not meant to be limiting, nor to mean that such parts of the disclosed retractable multi-use cardiac monitor are in any particular position or orientation relative to the outside environment.

It is to be understood that both the foregoing brief description of the drawings and the following detailed description are exemplary and explanatory only, and are not restrictive of the invention. These and other features, aspects and advantages of the present invention will become apparent from the following description, and the accompanying exemplary embodiments shown in the drawings, which are briefly described below.

Applicant hereby incorporates by reference U.S. Patent Publication No. 2008/0097231, published Apr. 28, 2008 and titled Cardiac Event Monitoring System (see also U.S. patent application Ser. No. 11/550,759, filed Oct. 18, 2006). For example, and without limitation, the retractable multi-use cardiac monitor 110 as herein described may be used as a wearable electrode system (110 of U.S. Patent Publication No. 2008/0097231) within a cardiac event monitoring system (100 of U.S. Patent Publication No. 2008/0097231).

Cardiac event monitoring is a procedure that is conducted on patients who report symptoms that may be cardiac in origin, and that occur infrequently, such as, for example, three times or less in one week. Cardiac monitoring is performed by the sensing and storage of electrocardiogram (ECG) data that characterizes activity of a patient's heart by a "cardiac monitor." In some instances, "event monitoring" is used to detect clinically significant heart related events. Event monitoring may be performed by patient activation, whereby the patient senses a cardiac event and causes data to be recorded. In other embodiments of event monitoring, a cardiac monitor analyzes incoming ECG data, identifies a clinically significant ECG event, and stores data related to the detected ECG event (e.g. an event monitor may identify particular types of Arrhythmias). In some embodiments, the cardiac monitor's ability to analyze incoming ECG data allows the cardiac monitor to detect a cardiac condition where a patient is otherwise asymptomatic.

Another type of monitoring is "Holter" monitoring. Holter monitoring is directed to constant recording and storage of ECG data from a patient. The quality and amount of ECG data recorded and stored varies based on quality requirements and memory storage limitations. Another cardiac monitoring technology is mobile cardiac telemetry. Mobile cardiac telemetry cardiac monitors may be configured to perform various types of event monitoring as well as constant storage of ECG similar to a holter monitor. In some embodiments, mobile cardiac telemetry monitors operate using auto-push technology that is configured to automatically transmit collected data to a monitoring center. A patient generally carries a cardiac monitor during a testing period, which can last for several days or up to, for example, 30 days.

An embodiment of the invention text, as shown and described by the various figures and accompanying text, provides a retractable multi-use cardiac monitor.

FIG. 1 illustrates an example of a cardiac monitor system. Referring to FIG. 1, a cardiac monitor system 100 may include a base unit 105 (the cardiac monitor of the illustrated system of FIG. 1), and a retractable multi-use cardiac monitor 110. The retractable multi-use cardiac monitor 110 may include a processor and a memory. The processor may be a microcontroller or a microprocessor. The memory may be a RAM, EEPROM, FLASH, or any other suitable volatile or non-volatile storage medium or device. The base unit 105 may include a base connector 120 and a body 107 that may house the electrical components and may include a user interface. The retractable multi-use cardiac monitor 110 may collect ECG data from a patient and may provide that data to the base unit 105 through wireless communication by a wireless radio. In some embodiments, the retractable multi-use cardiac monitor 110 may store the collected ECG data in a memory of the retractable multi-use cardiac monitor 110 prior to transmission. The wireless communication between the retractable multi-use cardiac monitor 110 and the base unit 105 may be accomplished using any one of a variety of different wireless technologies including, for example, and without limitation, 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In an alternative embodiment, the communication between the retractable multi-use cardiac monitor 110 and the base unit 105 may be wired.

Further, in some embodiments the retractable multi-use cardiac monitor 110 may be powered by a battery, while in other embodiments the retractable multi-use cardiac monitor 110 may be powered by a wired connection to base unit 105. In yet further embodiments, the retractable multi-use cardiac monitor 110 may collect other biological data, such as temperature, and may provide such data to base unit 105 by a wireless radio or through a wired connection, as discussed above, which may be further transmitted as discussed in reference to FIG. 2C or viewed by a health care professional as discussed below.

Figure 2A:
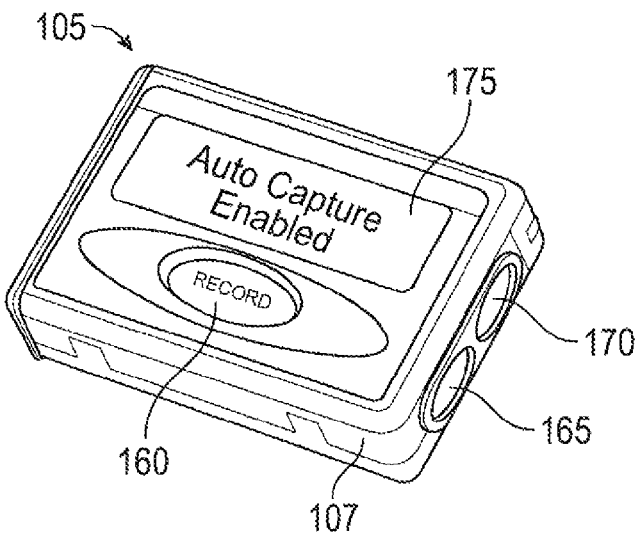
FIG. 2A is an illustration of a cardiac monitor system, according to one embodiment.
Figure 2B:
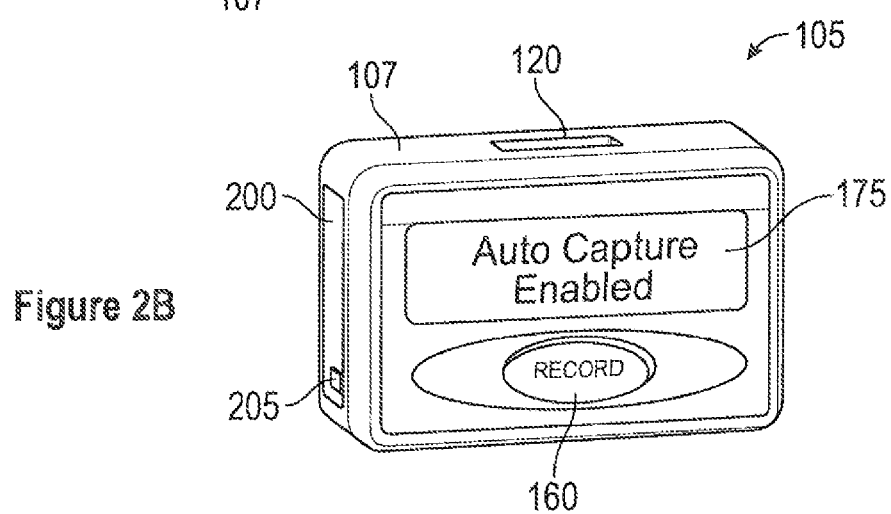
FIG. 2B is an illustration of a cardiac monitor system, according to one embodiment.

Referring now to FIGS. 1, 2A and 2B, the base unit 105 may be pager-sized, and may be either handheld or patient-worn. The base unit 105 may include the body 107 that may house components that may control operation of the cardiac monitor system 100. Thus, the base unit 105 may include a controller 150 within the body 107, and various input and output devices that may be coupled to the controller 150 through the body 107. The controller 150 may receive power from a power source 155 that may be provided by batteries that may be placed within a compartment 200 on a side of the body 107. The body 107 and the battery compartment 200 may be made of a suitable non-conductive lightweight material, such as a rigid plastic. The power source 155 may be turned off and on by a switch 205 (FIGS. 1 and 2B) accessible on the compartment 200 and connected to the power source 155 and the controller 150.

The controller 150 may include a processor 151, memory 152, a clock 153, and a counter 154 to process signals from the retractable multi-use cardiac monitor 110, receive input from a patient or a service technician using the system 100, and transmit recorded data to a monitoring center, as provided by a health professional, a clinic, or a hospital. In an alternative embodiment, input received from the retractable multi-use cardiac monitor 110 may be retained by the base unit 105 and displayed on the base unit 105 at a later time. For example, the input received from the retractable multi-use cardiac monitor 110 may later be shown to a doctor or other health professional during a patient visit. In some embodiments, the base unit 105 both may transmit collected data to a monitoring center and may retain collected data for later display or use.

The input devices on the base unit 105 may include a symptom record button 160, a yes/transmit button 165, and a no button 170. The yes/transmit button 165 may be used in one of two ways: it may be used as a response button to answer "yes" when queried by the controller 150, or it may be used to indicate to the controller 150 to transmit the ECG. The no button 170 may be used in one of two ways: it may be used as a response button to answer "no" when queried by the controller 150, or it may be used to indicate to the controller 150 to cancel a transmission of an ECG.

The output devices on the base unit 105 may include a display 175 such as a liquid crystal display (LCD) that may provide an interface with the patient and/or a technician, and a speaker 180 for transmitting data regarding the recording. For example, the display 175 may be used to show data collected from the retractable multi-use cardiac monitor 110 to a health care professional during a patient visit.

The system 100 may be worn for days or weeks, as it may be intended for use by patients who are experiencing symptoms that are transient and infrequent in nature. The base unit 105 may be worn outside the patient's clothing if there is any chance that moisture (for example, sweat) might come in contact with the base unit 105. The base unit 105 may be worn under outer wear, such as raincoats or jackets, for protection during wet or cold conditions. In one embodiment, the base unit 105 may operate as a Holter monitor, or may operate as an event monitor. In an alternative embodiment, the base unit 105 may operate as a mobile cardiac telemetry monitor. In some embodiments, the base unit 105 may operate as both a Holter monitor and an event monitor.

Figure 2C:
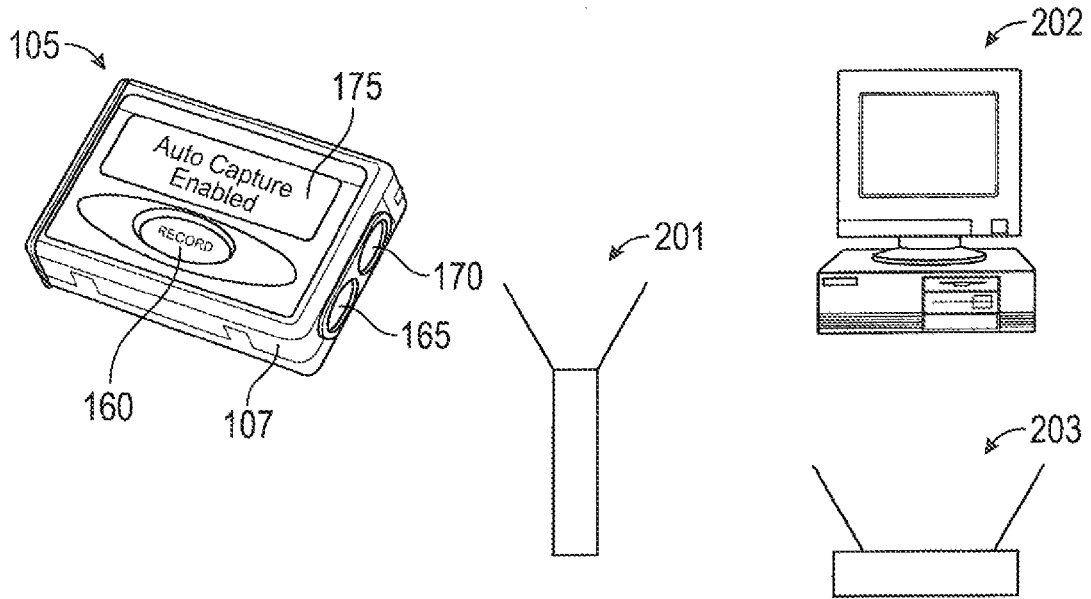
FIG. 2C is an illustration of a cardiac monitor system, according to one embodiment.

FIG. 2C illustrates various communication schemes for the base unit 105. In some embodiments, the base unit 105 may transmit data to a monitoring center, as provided by a health professional, a clinic, or a hospital by communicating with a cellular tower 201 of a cellular network. In an alternative embodiment, the base unit 105 may transmit data to a monitoring center by communicating with a computer 202 that may include an application which stores and forwards the data to the monitoring center through the Internet (e.g. by email). The application on computer 202 may also be configured to allow a user of the base unit 105 to print reports of the data collected by the base unit 105. Communication with the computer 202 may be wired or wireless. For example, the base unit 105 may plug into the computer 202 using a USB or firewire cable. In an alternative embodiment, the base unit 105 may communicate with the computer 202 through a variety of different wireless technologies including but not limited to 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In another embodiment, the base unit 105 may simply communicate with a wireless router 203 which may then communicate to the monitoring center through the Internet. The wireless router 203 may support any number of wireless technologies including, for example, and without limitation, IEEE 802.11 (Wi-Fi). In a related embodiment, the base unit 105 may be configured to detect the presence of the wireless router 203, and when the presence of the wireless router 203 is detected, the base unit 105 opportunistically may transmit collected data to the wireless router 203 which then may transmit the data to the monitoring center. In yet another embodiment, the base unit 105 may be configured to transmit data to a monitoring center over a telephone connection by audio modulation through the speaker 180. In yet further embodiments, the base unit 105 may transmit collected data to the monitoring center through any number of intermediaries and through any number of communication technologies.

Figure 3A:
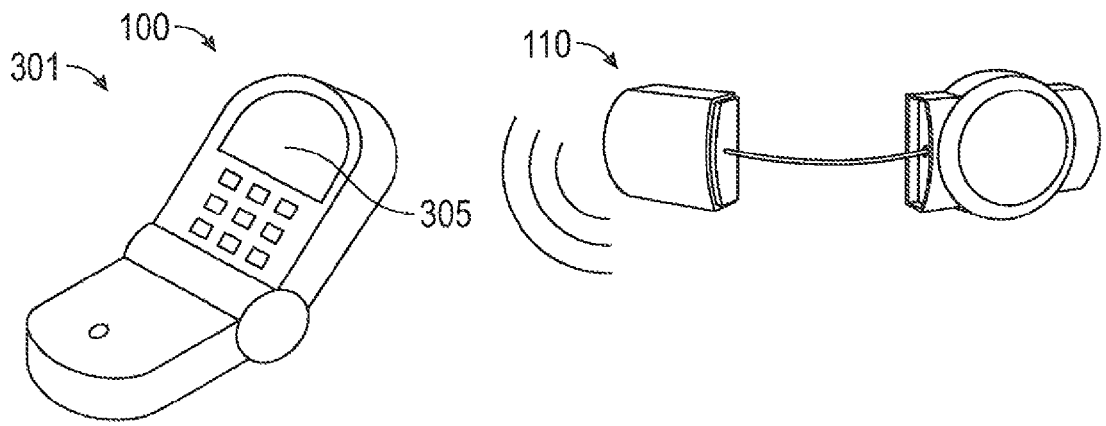
FIG. 3A is an illustration of a cardiac monitor system, according to one embodiment.

FIG. 3A illustrates an alternative embodiment where a cardiac monitoring system 100 may be comprised of a smart phone 301 (the cardiac monitor of the illustrated system of FIG. 3A) as well as a retractable multi-use cardiac monitor 110. The smart phone 301 may include a processor and a memory (not illustrated as they are within the smart phone 301). The smart phone 301 also may include a display screen 305. In the disclosed embodiment, the retractable multi-use cardiac monitor 110 may transmit collected ECG data to the smart phone 301. In some embodiments, the retractable multi-use cardiac monitor 110 may store the collected ECG data in a memory of the retractable multi-use cardiac monitor 110 prior to transmission. The smart phone 301 may operate as a Holter monitor, or may operate as an event monitor. In an alternative embodiment, the smart phone 301 may operate as a mobile cardiac telemetry monitor. In some embodiments, the smart phone 301 may operate as both a Holter monitor and an event monitor. In one embodiment, the retractable multi-use cardiac monitor 110 may wirelessly transmit collected ECG data to the smart phone 301 by a wireless radio. The wireless communication between the retractable multi-use cardiac monitor 110 and the smart phone 301 may be accomplished using any one of a variety of different wireless technologies including, for example, and without limitation, 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In an alternative embodiment, the communication between the retractable multi-use cardiac monitor 110 and the smart phone 301 may be wired. Further, in some embodiments, the retractable multi-use cardiac monitor 110 may be powered by a battery, while in other embodiments the retractable multi-use cardiac monitor 110 may be powered by a wired connection to smart phone 301. As noted above, the retractable multi-use cardiac monitor 110 may include a processor and a memory. The processor may be a microcontroller or a microprocessor. The memory may be a RAM, EEPROM, FLASH, or any other suitable volatile or non-volatile storage medium or device. In yet further embodiments, the retractable multi-use cardiac monitor 110 may collect other biological data, such as temperature, and may provide such data to the smart phone 301 by a wireless radio or through a wired connection as discussed above, which may be further transmitted as discussed in reference to FIG. 3B or viewed by a health care professional as discussed below.

The smart phone 301 may be configured to transmit data to a monitoring center, as provided by a health professional, a clinic, or a hospital. In an alternative embodiment, input received from the retractable multi-use cardiac monitor 110 may be retained by the smart phone 301 and may be displayed on the smart phone 301 at a later time or may be used at a later time. For example, the input received from the retractable multi-use cardiac monitor 110 may later be shown to a doctor or other health professional during a patient visit on the display screen 305 of the smart phone 301. In some embodiments, the smart phone 301 both may transmit collected data to a monitoring center and may retain collected data for later display or use.

Figure 3B:
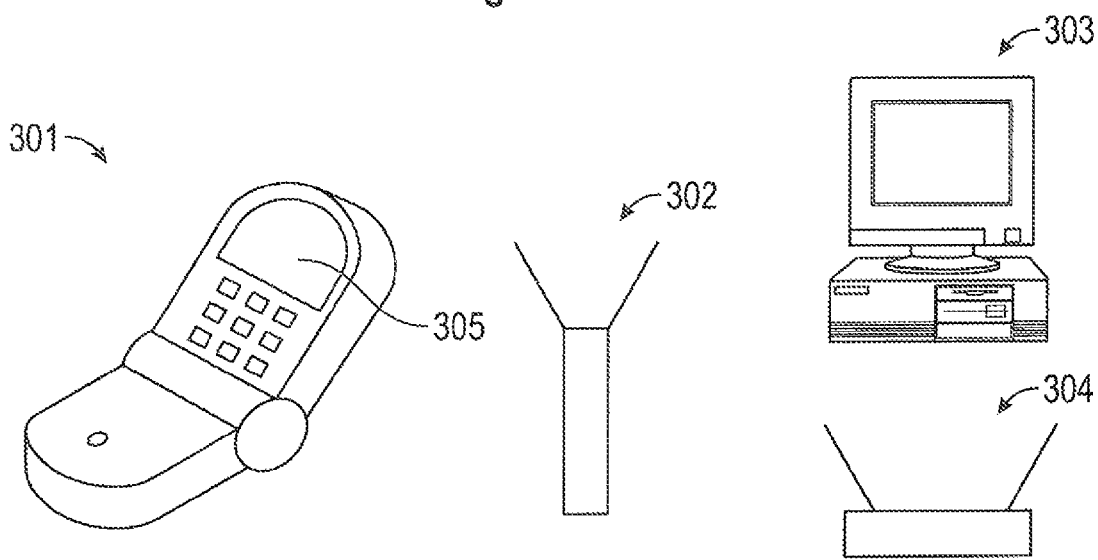
FIG. 3B is an illustration of a cardiac monitor system, according to one embodiment.

FIG. 3B illustrates various communication schemes for the smart phone 301. In some embodiments, the smart phone 301 may transmit data collected from the retractable multi-use cardiac monitor 110 to a monitoring center, as provided by a health professional, a clinic, or a hospital by communicating with a cellular tower 302 of a cellular network. In an alternative embodiment, the smart phone 301 may transmit data to a monitoring center by communicating with a computer 303 that may include an application which stores and forwards the data to the monitoring center through the Internet (e.g. by email). The application on computer 303 may also be configured to allow a user of the smart phone 301 to print reports of the ECG data collected by the smart phone 301. Communication with the computer 302 may be wired or wireless. For example, and without limitation, the smart phone 301 may plug into the computer using a USB or firewire cable. In an alternative embodiment, the smart phone 301 may communicate with the computer 303 through a variety of different wireless technologies including, for example, and without limitation, 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In another embodiment, the smart phone 301 simply may transmit collected data to a wireless router 304 which then may transmit the data to the monitoring center through the Internet. The wireless router 304 may support any number of wireless technologies including, for example, and without limitation, IEEE 802.11 (Wi-Fi). In a related embodiment, the smart phone 301 may be configured to detect the presence of the wireless router 304, and when the presence of the wireless router 304 is detected, the smart phone 301 opportunistically may transmit collected data to the wireless router 304 which then may transmit the data to the monitoring center. In yet another embodiment, the smart phone 301 may be configured to transmit data to a monitoring center over a telephone connection by audio modulation. In yet further embodiments, the smart phone 301 may transmit collected data to the monitoring center through any number of intermediaries and through any number of communication technologies.

Regarding the transmission of data, the retractable multi-use cardiac monitor 110 may store collected data on an on-board memory and may "push" the data to a cardiac monitor (e.g. base unit 105 of FIG. 1 or smart phone 301 of FIG. 3A). Alternatively, the retractable multi-use cardiac monitor 110 may store collected data on an on-board memory and may be designed to await a request from a cardiac monitor (e.g. base unit 105 of FIG. 1 or smart phone 301 of FIG. 3A) to "pull" data from the retractable multi-use cardiac monitor 110. Further, the retractable multi-use cardiac monitor 110 may be configured to stream data as it is collected directly to a cardiac monitor (e.g. base unit 105 of FIG. 1 or smart phone 301 of FIG. 3A).

Figure 3C:
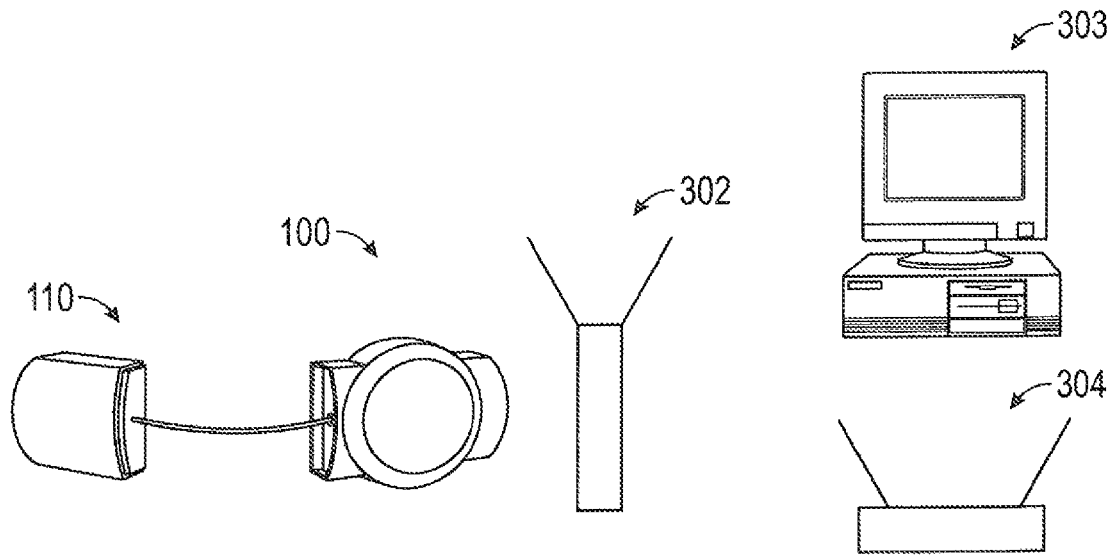
FIG. 3C is an illustration of a cardiac monitor system, according to one embodiment.

FIG. 3C illustrates an embodiment where the multi-use cardiac monitor 110 itself may comprise the entire cardiac monitoring system 100. The multi-use cardiac monitor 110 may operate as a Holter monitor, or may operate as an event monitor. In an alternative embodiment, the multi-use cardiac monitor 110 may operate as a mobile cardiac telemetry monitor. In some embodiments, the multi-use cardiac monitor 110 may operate as both a Holter monitor and an event monitor. In some embodiments, the multi-use cardiac monitor 110 may be configured to transmit collected ECG data to a monitoring center, as provided by a health professional, a clinic, or a hospital. In some embodiments, the retractable multi-use cardiac monitor 110 may store the collected ECG data in a memory of the retractable multi-use cardiac monitor 110 prior to transmission. In an alternative embodiment, the retractable multi-use cardiac monitor 110 may include a display screen and the retractable multi-use cardiac monitor 110 may retain any collected ECG data and may display the collected ECG data at a later time. For example, and without limitation, the collected ECG data may later be shown to a doctor or other health professional during a patient visit on a display screen (e.g., 2101 or FIG. 21 or 2201 of FIG. 22) of the retractable multi-use cardiac monitor 110. In some embodiments, the retractable multi-use cardiac monitor 110 both may transmit collected ECG data to a monitoring center and may retain collected ECG data for later display. As noted above, the retractable multi-use cardiac monitor 110 may include a processor and a memory. The processor may be a micro controller or a microprocessor. The memory may be a RAM, EEPROM, FLASH, or any other suitable volatile or non-volatile storage medium or device. In yet further embodiments, the retractable multi-use cardiac monitor 110 may collect other biological data, such as temperature, and may transmit such data as discussed above and below, and may retain the data for later display or use.

FIG. 3C also illustrates various communication schemes for the retractable multi-use cardiac monitor 110 where it comprises the entire cardiac monitor system 100. In some embodiments, the retractable multi-use cardiac monitor 110 may transmit collected data to a monitoring center, as provided by a health professional, a clinic, or a hospital by communicating with a cellular tower 302 of a cellular network by a wireless radio. In an alternative embodiment, the retractable multi-use cardiac monitor 110 may transmit data to a monitoring center by communicating with a computer 303 that may include an application which stores and forwards the data to the monitoring center through the Internet (e.g. by email). The application on computer 303 may also be configured to allow a user of the retractable multi-use cardiac monitor 110 to print reports of the data collected by the retractable multi-use cardiac monitor 110. Communication with the computer 302 may be wired or wireless by a wireless radio. For example, and without limitation, the retractable multi-use cardiac monitor 110 may plug into the computer using a USB or firewire cable. In an alternative embodiment, the retractable multi-use cardiac monitor 110 may communicate with the computer 303 through a variety of different wireless technologies including, for example, and without limitation, 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In another embodiment, the retractable multi-use cardiac monitor 110 by a wireless radio simply may transmit collected data to a wireless router 304 which then may transmit the data to the monitoring center through the Internet. The wireless router 304 may support any number of wireless technologies including, for example, and without limitation, IEEE 802.11 (Wi-Fi). In a related embodiment, the retractable multi-use cardiac monitor 110 may be configured to detect the presence of the wireless router 304, and when the presence of the wireless router 304 is detected, the retractable multi-use cardiac monitor 110 opportunistically may transmit collected data by a wireless radio to the wireless router 304 which then may transmit the data to the monitoring center. In yet another embodiment, the retractable multi-use cardiac monitor 110 may be configured to transmit data to a monitoring center over a telephone connection by audio modulation. In yet further embodiments, the retractable multi-use cardiac monitor 110 may transmit collected data to the monitoring center through any number of intermediaries and through any number of communication technologies.

Figure 4:
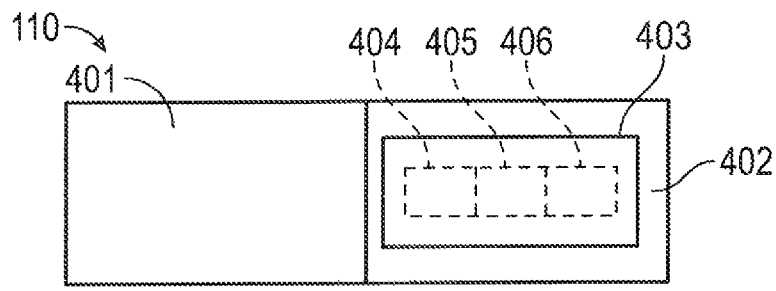
FIG. 4 is a top-down view of a retractable multi-use cardiac monitor, according to one embodiment.

FIG. 4 is a top-down view of a retractable multi-use cardiac monitor 110, according to one embodiment. The retractable multi-use cardiac monitor 110 may include left 401 and right sides 402 each comprised of a left and right side housing (also referenced as 401 and 402 respectively). The retractable multi-use cardiac monitor 110 may be comprised of anyone of a number of different materials including, for example, and without limitation, plastic and metal. The illustrated embodiment of FIG. 1 includes a symptom button 403 on the right 402 side of the retractable multi-use cardiac monitor 110. In one embodiment, the symptom button 403 may be used by the patient to "wake up" the cardiac monitor with which the retractable multi-use cardiac monitor 110 is associated, such that the cardiac monitor may begin recording data as either a Holter or event or mobile cardiac telemetry (MCT) monitor depending on the cardiac monitor's configuration. In an alternative embodiment, the symptom button 403 may be used to indicate that a cardiac "event" has occurred, and the retractable multi-use cardiac monitor 110 may begin to record data relative to the "event." In various alternative embodiments, the symptom button 403 may be used as an input to the retractable multi-use cardiac monitor 110, a cardiac monitor with which the retractable multi-use cardiac monitor 110 is associated, or any other portion of a system with which the retractable multi-use cardiac monitor 110 is associated. In an alternative embodiment, the symptom button 403 may be disposed on the left 401 side of the retractable multi-use cardiac monitor 110. The embodiment of FIG. 4 also illustrates each of a processor 404, a memory 405, and a wireless radio 406. Each of processor 404, memory 405, and wireless radio 406 are illustrated with dashed lines because they lie below the outer surface of the right side housing 402 and within the right side housing 402. One of skill in the art would appreciate that each of the processor 404, memory 405, and wireless radio 406 may be placed in various locations within the retractable multi-use cardiac monitor 110. For example, and without limitation, processor 404 could be included in the left side housing 401. As noted above, each of the processor 404, memory 405, and wireless radio 406 may be of various types in various embodiments.

Figure 5:
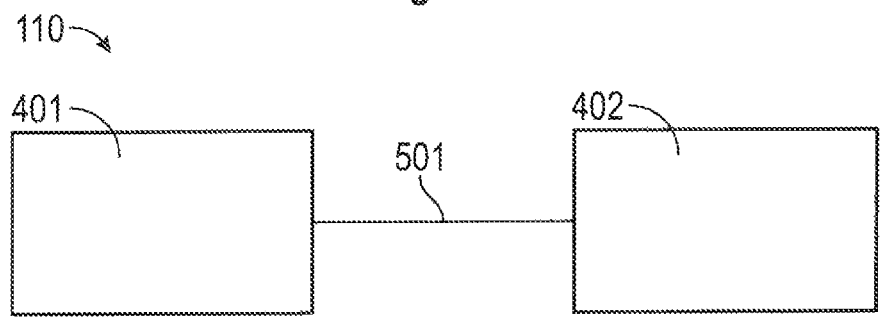
FIG. 5 is a top-down view of a retractable multi-use cardiac monitor, according to one embodiment.

FIG. 5 is also a top-down view of a retractable multi-use cardiac monitor 110, according to one embodiment of the present invention. The embodiment of FIG. 5 illustrates a retractable wire 501 that may connect the left 401 and right 402 sides of the retractable multi-use cardiac monitor 110. The wire 501 may be fiber-optic or electrical. Further, the wire 501 may be shielded or non-shielded. In one embodiment, the wire 501 may retract into the right side 402. In another embodiment, the wire 501 may retract into the left side 401. In both embodiments, the left 401 and right 402 sides of retractable multi-use cardiac monitor 110 may be extended away from and retracted toward one another. The retractable nature of the retractable multi-use cardiac monitor 110 may advantageously allow for easy and convenient storage of the wire 501.

Figure 6:
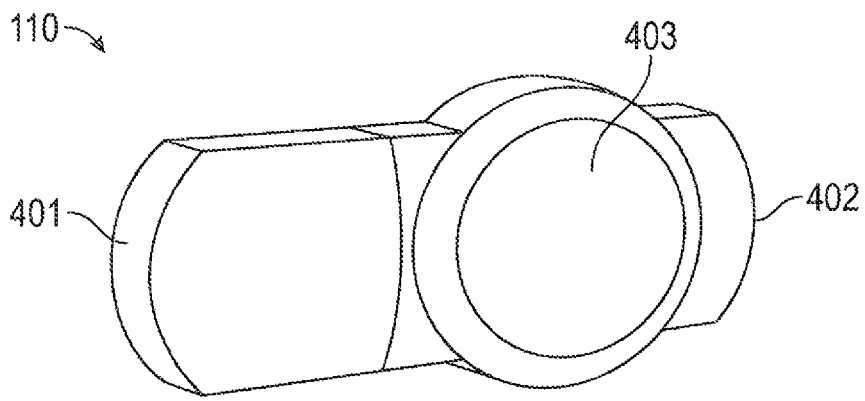
FIG. 6 is a top-down view of a retractable multi-use cardiac monitor, according to one embodiment.
Figure 6:
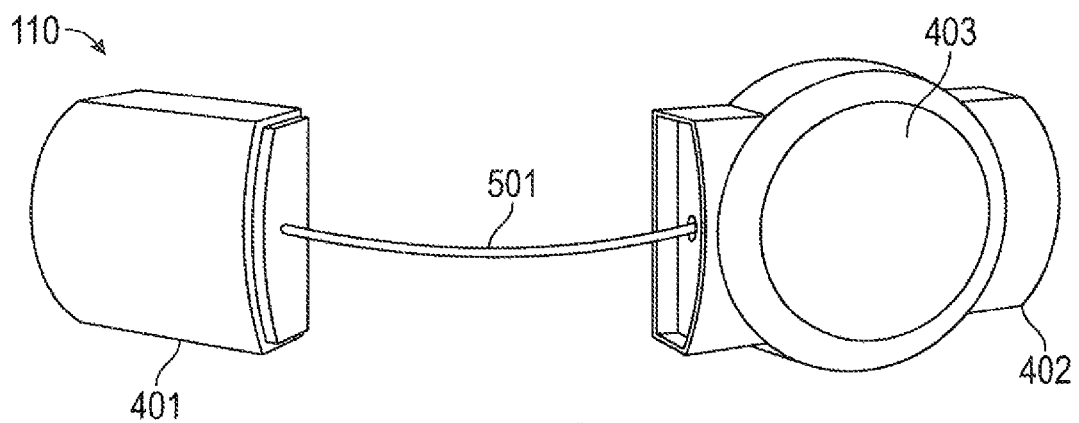

FIG. 6 is yet another illustration of an embodiment of a retractable multi-use cardiac monitor 110. The illustrated embodiment includes left 401 and right 402 sides, as well as a retractable wire 501. The illustrated embodiment also includes a symptom button 403 on the right side 402 of the retractable multi-use cardiac monitor 110.

Figure 7:
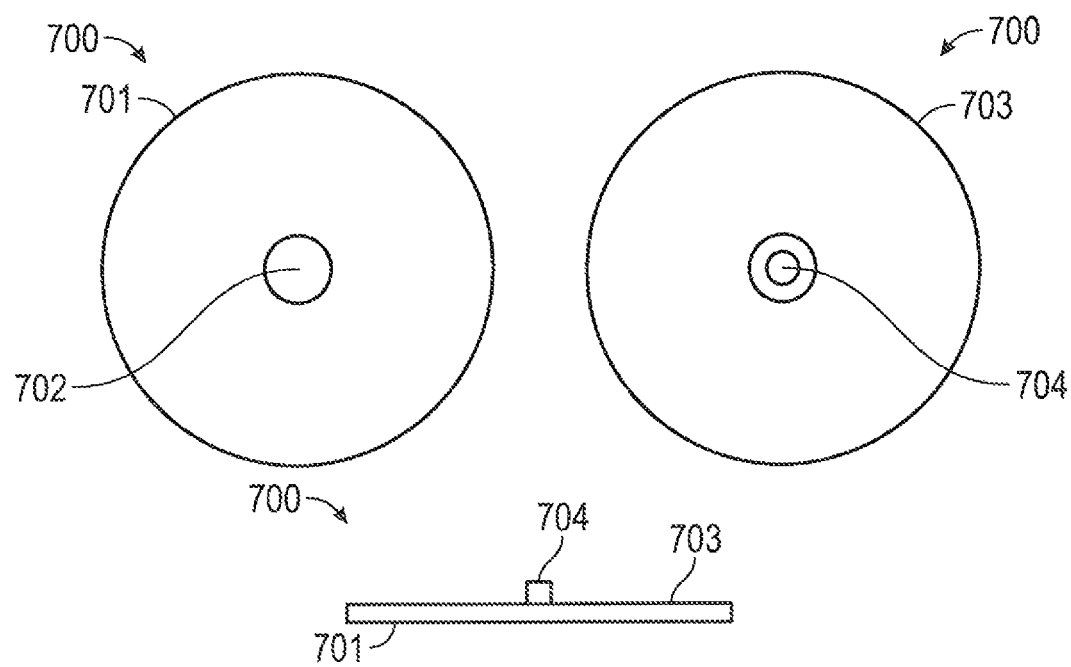
FIG. 7 is an illustration of a wearable electrode, according to one embodiment.

FIG. 7 is a top-down view of a wearable electrode 700, according to one embodiment of the present invention. The wearable electrode 700 may be comprised of an electrode contact 702 that may be configured to contact skin. The wearable electrode 700 may detect electrical signals from a patient's heart through the electrode contact 702. The wearable electrode 700 also may include a top surface 703, as well as a bottom surface 701 that may include adhesive to facilitate connection of the wearable electrode 700 to skin. The wearable electrode 700 also may include a connector 704 to allow the wearable electrode to be connected to a device. The connector 704 is illustrated as a metal post. In some embodiments, the bottom surface 701 may also be coated with a gel that may improve electrical conduction between the patient's skin and the electrode contact 702.

Figure 8:
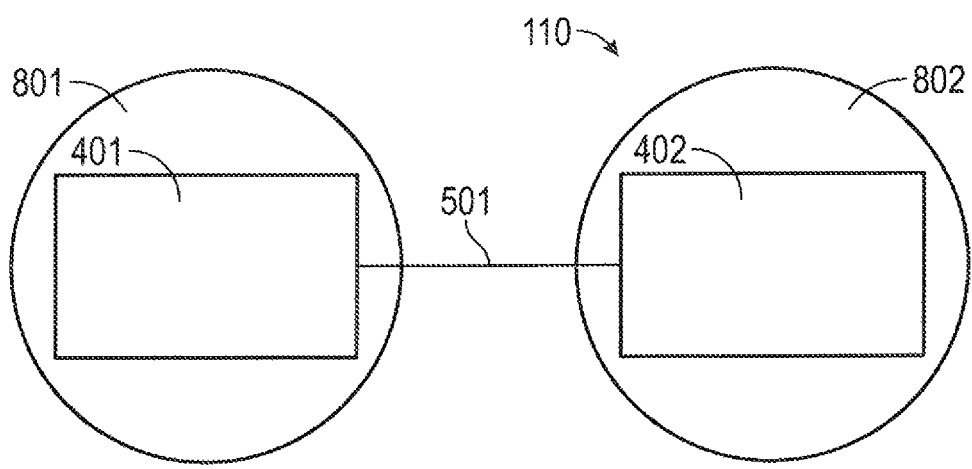
FIG. 8 is a top-down view of a retractable multi-use cardiac monitor with wearable electrodes attached, according to one embodiment.
Figure 9:
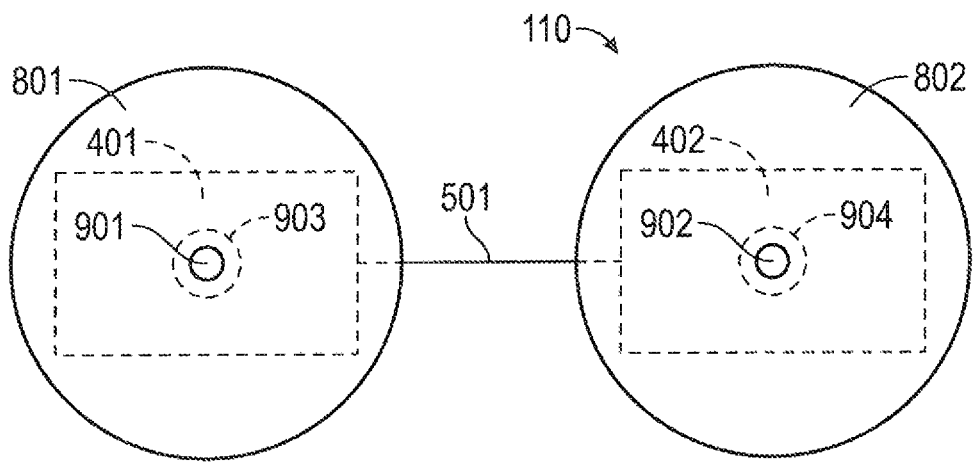
FIG. 9 is a bottom-up view of a retractable multi-use cardiac monitor with wearable electrodes attached, according to one embodiment.

FIG. 8 is a top-down view of a retractable multi-use cardiac monitor 110 with wearable electrodes (left 801 and right 802) attached, according to one embodiment of the present invention. FIG. 9 is a bottom-up view of a retractable multi-use cardiac monitor 110 with wearable electrodes (left 801 and right 802) attached, according to one embodiment. The left wearable electrode 801 may include a left electrode contact 901 and the right wearable electrode 802 may include a right electrode contact 902. The left 801 and right 802 wearable electrodes may connect to the left 401 and right 402 sides of the retractable multi-use cardiac monitor 110 by connection to the left 903 and right 904 sensing connectors. By way of example, FIG. 7 illustrates a connector 704 for a wearable electrode 700. In one embodiment, the sensing connectors (903 and 904) may be configured to accept the connector post 704 for connection to a wearable electrode.

As discussed above with respect to FIG. 7, these wearable electrodes may be configured to contact the skin of a patient to detect electrical signals of the patient's heart through the electrode contacts. In one embodiment, the wearable electrodes (left 801 and right 802) and consequently the electrode contacts (left 901 and right 902) may be designed to be temporarily placed against the patient's skin by the patient to detect a small amount of ECG data. For example, a patient may not be feeling well, and may desire to make a short recording of ECG data by holding the wearable electrodes (left 801 and right 802) of the retractable multi-use cardiac monitor 110 against his skin for short period. In another embodiment, the wearable electrodes (left 801 and right 802) and consequently the electrode contacts (left 901 and right 902) may be designed to be attached for an extended period of time. As discussed above, in some embodiments an adhesive may be provided for wearable electrodes, which may facilitate the attachment of the left 801 and right 802 wearable electrodes for an extended period of time. The left 401 and right 402 sides of the retractable multi-use cardiac monitor 110 are shown as dashed lines in this bottom-up view because they are disposed behind the left 801 and right 802 wearable electrodes. Similarly, the left 903 and right 904 sensing connectors are shown as dashed lines in this bottom-up view because they are disposed behind the left 801 and right 802 wearable electrodes. The left 903 and right 904 sensing connectors, or the combination of the left 801 and right 802 wearable electrodes with the left 903 and right 904 sensing connectors, collect ECG and other biological data.

Figure 10:
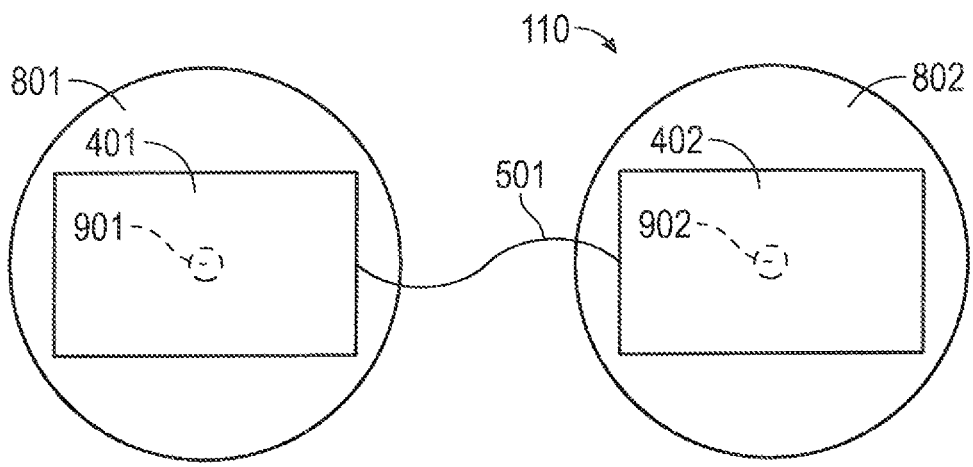
FIG. 10 is a top-down view of a retractable multi-use cardiac monitor with wearable electrodes attached, according to one embodiment.

FIG. 10 is a top-down view of a retractable multi-use cardiac monitor with wearable electrodes (left 801 and right 802) attached. The FIG. 10 embodiment illustrates that the wire 501 may be flexible, and may move flexibly in any direction. FIG. 10 illustrates the left 901 and right 902 electrode contacts as dashed lines in this top-down view because they are disposed behind the left 401 and right 402 sides, as well as the left 801 and right 802 wearable electrodes, respectively.

Figure 11:
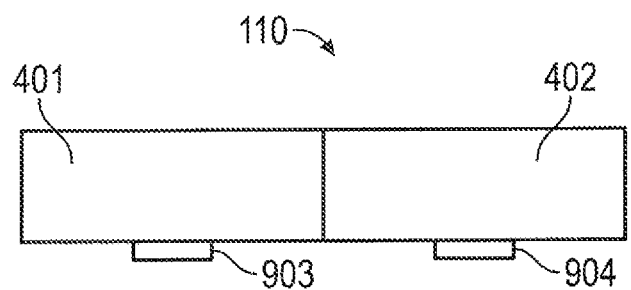
FIG. 11 is a side-view of a retractable multi-use cardiac monitor, according to one embodiment.

FIG. 11 is a side-view of a retractable multi-use cardiac monitor 110, according to one embodiment of the present invention. FIG. 11 illustrates left 903 and right 904 sensing connectors which protrude away from the left 401 and right 402 sides of the retractable multi-use cardiac monitor 110.

Figure 12:
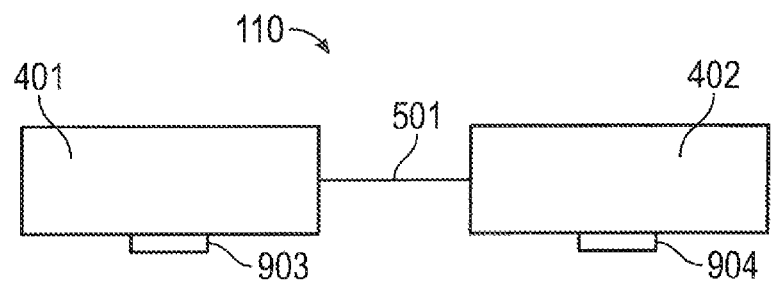
FIG. 12 is a side-view of a retractable multi-use cardiac monitor, according to one embodiment.
Figure 13:
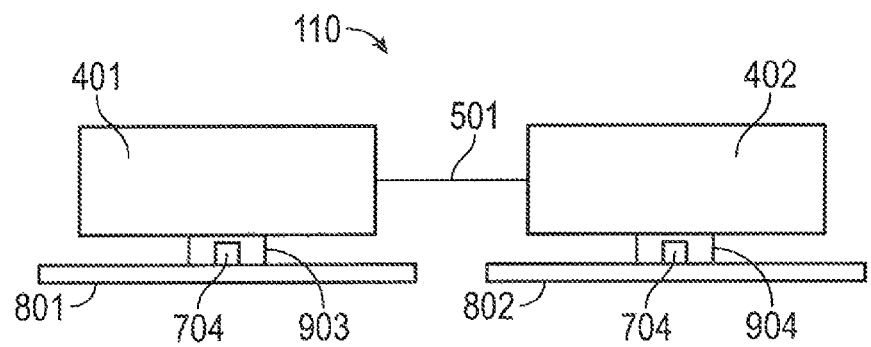
FIG. 13 is a side-view of a retractable multi-use cardiac monitor with wearable electrodes attached, according to one embodiment.

FIG. 12 is a side-view of a retractable multi-use cardiac monitor 110, according to one embodiment of the present invention. FIG. 12 illustrates the extractable wire 501 that connects the left 401 and right 402 sides of the retractable multi-use cardiac monitor 110. FIG. 13 is a side-view of a retractable multi-use cardiac monitor 110 with wearable electrodes (left 801 and right 802) attached, according to one embodiment. FIG. 13 similarly illustrates the extractable wire 501 that connects the left 401 and right 402 sides of the retractable multi-use cardiac monitor 110. FIG. 13 also illustrates an embodiment in which the sensing connectors 903 and 904 are configured to accept a connector post 704 for wearable electrodes 801 and 802.

Figure 14A:
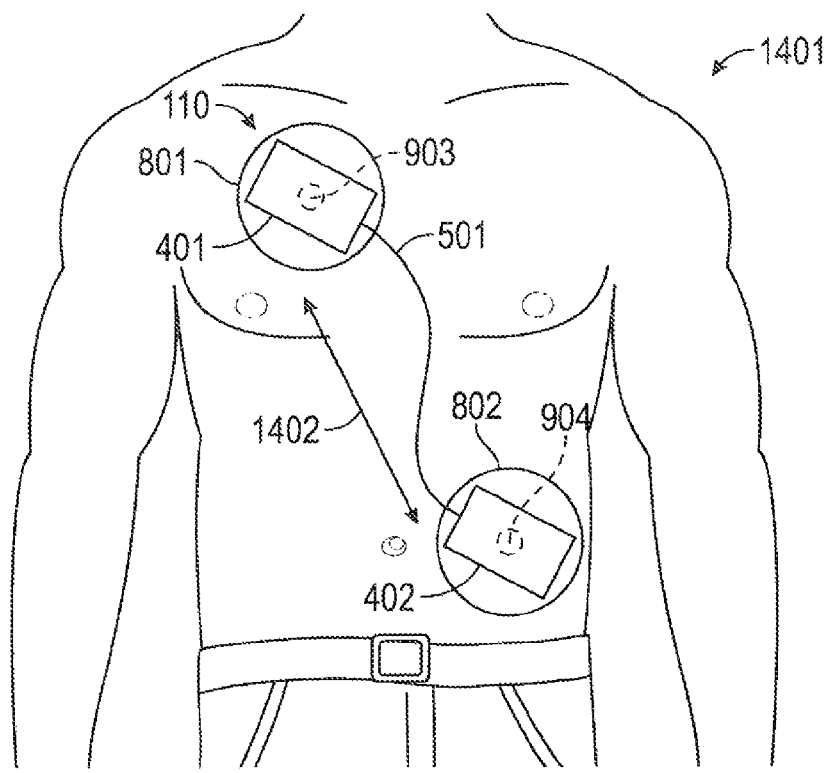
FIG. 14A is an illustration of a retractable multi-use cardiac monitor attached to a cardiac monitoring patient, according to one embodiment.

FIG. 14A is an illustration of a retractable multi-use cardiac monitor 110 attached to a cardiac monitoring patient 1401, according to one embodiment of the present invention. The multi-use cardiac monitor 110 may be configured to collect ECG signals through the left 801 and right 802 wearable electrodes that are connected to the patient's 1401 skin. FIG. 14A illustrates a distance 1402 between the left 401 and right 402 sides of the retractable multi-use cardiac monitor 110. As discussed above with respect to FIG. 5, the retractable multi-use cardiac monitor 110 may be configured to allow the left 401 and right 402 sides to be extended away from and retracted toward one another. As discussed above with respect to FIG. 5, the retractable nature of the wire 501 also may advantageously allow for easy storage of the wire 501.

Furthermore, the retractable wire 501 may advantageously allow the distance 1402 between the left 401 and right 402 sides of the retractable multi-use cardiac monitor 110 to be variable. The variable nature of the distance 1402 between the left 401 and right 402 sides may allow a user of the retractable multi-use cardiac monitor 110 to adjust the distance between the left 801 and right 802 wearable contact electrodes that are connected to the patient's 1401 skin and are used to collect ECG signals. Similarly, the variable nature of the distance 1402 may allow a user to adjust the vector length between the corresponding left 903 and right 904 sensing connectors to which the left 801 and right 802 wearable contact electrodes are attached. The distance 1402 may be adjusted by the patient 1401 to achieve an optimum electrode vector length between the left 903 and right 904 sensing connectors for ECG signal collection. In some embodiments, the retractable multi-use cardiac monitor 110 alone or in combination with another cardiac monitor may be configured to assist the patient 1401 with the determination of an optimum electrode vector length.

Interelectrode distance (vector length) significantly affects the strength and fidelity of detected ECG signals. Various studies have been conducted that analyze the effect of inter electrode distance (vector length) on collected ECG signals. See M. Puurtinen, et al., *Estimation of ECG Signal of closely separated bipolar electrodes using thorax models*, Proceedings of the 26th Annual International Conference of the IEEE EMBS pp. 801-804, San Francisco, Calif., USA, Sep. 1-5, 2004, which is herein incorporated by reference in its entirety.

Figure 14B:
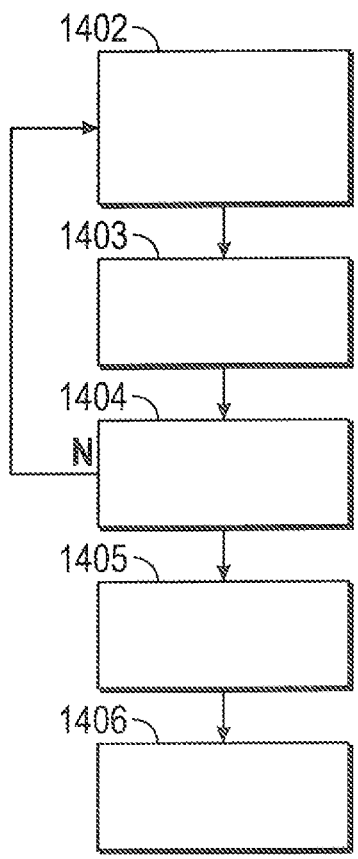
FIG. 14B is a flowchart illustrating the determination of an optimum electrode vector length, according to one embodiment.

FIG. 14B is a flowchart illustrating the determination of an optimum electrode vector length, according to one embodiment of the present invention. The FIG. 14B flowchart illustrates the steps of optimum electrode vector length determination from the perspective of a cardiac monitor (e.g. base unit 105 of FIG. 1 or smart phone of FIG. 3A), in an embodiment where a retractable multi-use cardiac monitor 110 may be used with another cardiac monitor to determine the optimum electrode vector length between the left 903 and right 904 sensing connectors. In step 1402, data may be received by the cardiac monitor (e.g. base unit 105 of FIG. 1 or smart phone of FIG. 3A) from the retractable multi-use cardiac monitor 110 representing a distance between the left 401 and right 402 sides of the retractable multi-use cardiac monitor 110 (and consequently left 903 and right 904 sensing connectors). In step 1403, ECG data collected by the retractable multi-use cardiac monitor 110 at the current distance between the left 401 and right 402 sides may be received by the cardiac monitor (e.g. base unit 105 of FIG. 1 or smart phone of FIG. 3A). In step 1404, the received ECG collected data and the data representing the distance between the left 401 and right 402 sides may be recorded by the cardiac monitor (e.g. base unit 105 of FIG. 1 or smart phone of FIG. 3A). The received ECG collected data and the data representing the distance between the left 401 and right 402 may be recorded in a memory. Steps 1402 through 1404 may be repeated a number of times N with various distances between the left 401 and right 402 sides of the retractable multi-use cardiac monitor 110. In some embodiments, the number of times N may be variable. In other embodiments, the number of times N may be constant. In yet other embodiments, the number of times N may be variable and depends on intermediate calculations performed from the collected ECG data and distance values. In step 1405, an optimum electrode vector length between the left 903 and right 904 sensing connectors may be calculated based on the ECG and distance data recorded in step 1404 by the processor of the cardiac monitor (e.g. by the processor of base unit 105 of FIG. 1 or the processor of smart phone 301 of FIG. 3A). In step 1406, a notification may be generated indicating the optimum electrode vector length has been found. The notification may be generated by the cardiac monitor (e.g. base unit 105 of FIG. 1 or smart phone of FIG. 3A) or the retractable multi-use cardiac monitor 110. In some embodiments, the notification may be an audible noise. In other embodiments, the notification may be visual such as by a light or a display on a visual display (e.g. 2101 of FIG. 21 or 2201 of FIG. 22) of the retractable multi-use cardiac monitor 110, or by a light or a visual display on the display of a cardiac monitor (e.g. on a display 175 of base unit 105 of FIG. 1 or a display 305 of smart phone 301 of FIG. 3A).

In one embodiment, an optimum electrode vector length may be calculated based on comparison of recorded signal strengths of ECG data at various vector distances collected by Steps 1402 through 1404. In another embodiment, an optimum electrode vector length may be calculated based on comparison of recorded signal fidelities of ECG data at various vector distances collected by Steps 1402 through 1404. In another embodiment, an optimum electrode vector length may be calculated based on comparison of both recorded signal strengths as well as recorded signal fidelities of ECG data at various vector distances collected by Steps 1402 through 1404. In yet other embodiments, an optimum electrode vector length may be calculated based on analyzing the ECG data at various vector distances collected by Steps 1402 through 1404 to determine if the collected ECG data represents a high fidelity QRS ECG pattern. In yet other embodiments, other signal quality measures are used to calculate an optimum vector length. The intermediate calculations noted above in reference to FIG. 14B may be any of these operations.

Figure 14C:
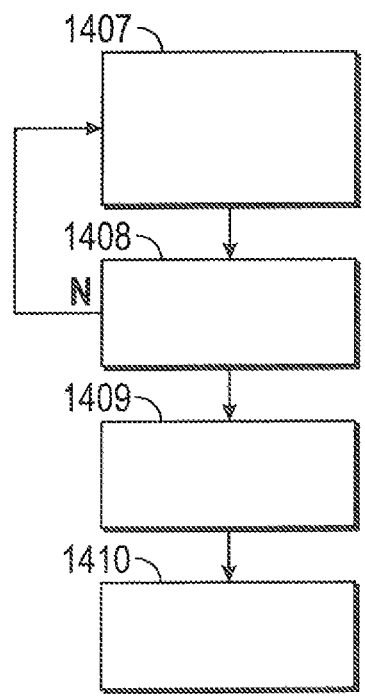
FIG. 14C is a flowchart illustrating the determination of an optimum electrode vector length, according to one embodiment.

FIG. 14C is a flowchart illustrating the determination of an optimum electrode vector length, according to one embodiment of the present invention. The FIG. 14C flowchart illustrates the steps of optimum electrode vector length determination from the perspective of a retractable multi-use cardiac monitor 110 in an embodiment where the retractable multi-use cardiac monitor 110 determines the optimum vector length between the left 903 and right 904 sensing connectors by itself. In step 1407, the retractable multi-use cardiac monitor 110 may determine a distance between the left 401 and right 402 sides (and consequently left 903 and right 904 sensing connectors) of the retractable multi-use cardiac monitor 110 and the retractable multi-use cardiac monitor 110 may record the distance. In step 1408, the retractable multi-use cardiac monitor 110 may collect and may record ECG data. The ECG data and distance between the left 401 and right 402 sides may be recorded in a memory of the retractable multi-use cardiac monitor 110. Steps 1407 and 1408 may be repeated a number of times N with various distances between the left 401 and right 402 sides. In some embodiments, the number of times N may be variable. In other embodiments, the number of times N may be constant. In yet other embodiments, the number of times N may be variable and may depend on intermediate calculations performed from the collected ECG data and distance between the left 401 and right 402 sides. In step 1409, an optimum electrode vector length between the left 903 and right 904 sensing connectors may be calculated based on the ECG data at various vector distances recorded in steps 1407 and 1408 by a processor of the retractable multi-use cardiac monitor 110. In step 1410, the retractable multi-use cardiac monitor 110 may generate a notification indicating the optimum electrode vector length has been found. In some embodiments, the notification may be an audible noise. In other embodiments, the notification may be visual such as by a light or a display on a display screen (e.g. 2101 of FIG. 21 or 2201 of FIG. 22) of the retractable multi-use cardiac monitor 110.

In one embodiment, an optimum electrode vector length may be calculated based on comparison of recorded signal strengths of ECG data at various vector distances collected by Steps 1407 and 1408. In another embodiment, an optimum electrode vector length may be calculated based on comparison of recorded signal fidelities of ECG data at various vector distances collected by Steps 1407 and 1408. In another embodiment, an optimum electrode vector length may be calculated based on comparison of both recorded signal strengths as well as recorded signal fidelities of ECG data at various vector distances collected by Steps 1407 and 1408. In yet other embodiments, an optimum electrode vector length may be calculated based on analyzing the ECG data at various vector distances collected by Steps 1407 and 1408 to determine if the collected ECG data represents a high fidelity QRS ECG pattern. In yet other embodiments, other signal quality measures may be used to calculate an optimum vector length. The intermediate calculations noted above in reference to FIG. 14C may be any of these operations.

Figure 14D:
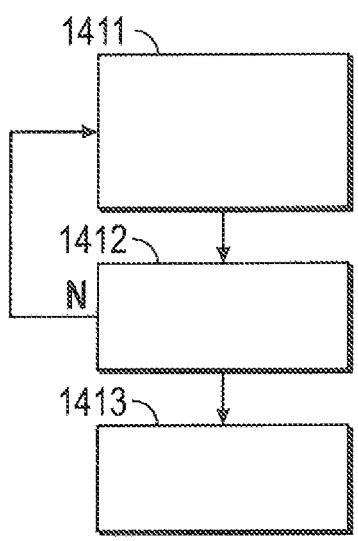
FIG. 14D is a flowchart illustrating the determination of an optimum electrode vector length, according to one embodiment.

FIG. 14D is a flowchart illustrating the determination of an optimum electrode vector length, according to one embodiment of the present invention. The FIG. 14D flowchart illustrates the steps of optimum electrode vector length determination from the perspective of a patient or a healthcare professional. In FIG. 14D, the retractable multi-use cardiac monitor 110 alone or in combination with another cardiac monitor may be configured to assist the patient or healthcare professional with the determination of an optimum electrode vector length as explained in FIGS. 14B and 14C above. In step 1411, the patient or healthcare professional may adjust a distance between the left 401 and right 402 sides of the retractable multi-use cardiac monitor 110. In step 1412, the patient or healthcare professional may hold the retractable multi-use cardiac monitor 110 against a portion of a patient body to record data. Steps 1411 and 1412 may be repeated a number of times N with various distances between the left 401 and right 402 sides. In some embodiments, the number of times N may be variable. In other embodiments, the number of times N may be constant. In yet other embodiments, the number of times N may be variable and may depend on intermediate calculations performed from the collected data and distance adjustments. In step 1413, the patient or healthcare professional may receive a notification of the optimum electrode vector length from either a cardiac monitor (e.g. base unit 105 of FIG. 1 or smart phone 301 of FIG. 3A) or from the retractable multi-use cardiac monitor 110, as explained above in the discussion of FIGS. 14B and 14C. In an alternative embodiment, the patient or healthcare professional may not receive a notification in step 1413. Rather, the patient or healthcare professional may review the iteratively collected ECG data at various vector distances to determine the optimum vector length. For example, the patient or healthcare professional may review such data on a display screen (e.g. 2101 of FIG. 21 or 2201 of FIG. 22) of the retractable multi-use cardiac monitor 110, or on a display screen of a cardiac monitor (e.g. display 175 of base unit 105 of FIG. 1 or display 305 of smart phone 301 of FIG. 3A).

Figure 14E:
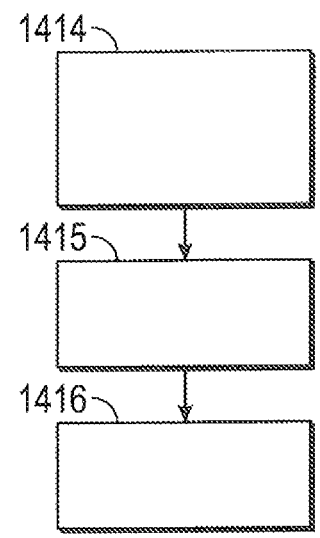
FIG. 14E is a flowchart illustrating the collection and transmission of data, according to one embodiment.

FIG. 14E is a flowchart illustrating the collection of and transmission of data, according to one embodiment of the present invention. In step 1414, the retractable multi-use cardiac monitor 110 may collect ECG or other biological data as described above. In some embodiments, ECG or biological data may be collected from more than two electrodes or sensing connectors as described, for example, and without limitation, in reference to FIGS. 17, 19, and 20 below. In step 1415, the collected data may be stored. The collected data may be stored in a memory of the retractable multi-use cardiac monitor 110. The collected data may be then transmitted as described in the various embodiments above to a destination.

Figure 15:
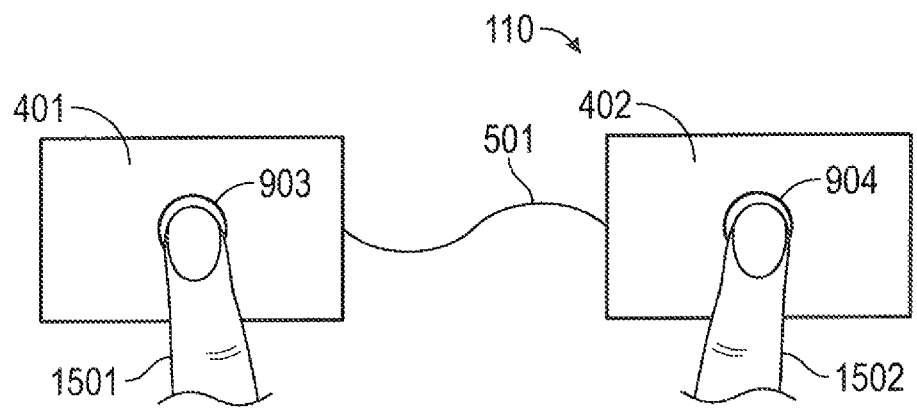
FIG. 15 is an illustration of a finger electrode configuration of a retractable multi-use cardiac monitor, according to one embodiment.
Figure 16:
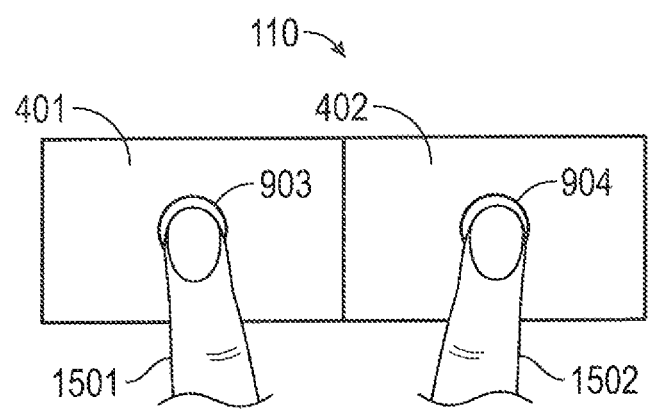
FIG. 16 is an illustration of a finger electrode configuration of a retractable multi-use cardiac monitor, according to one embodiment.

FIG. 15 is an illustration of a finger electrode configuration of the retractable multi-use cardiac monitor 110, according to one embodiment of the present invention. In the illustrated embodiment, a user of the retractable multi-use cardiac monitor 110 may place a left side finger 1501 and a right side finger 1502 onto the left 903 and right 904 sensing connectors, respectively. In the illustrated embodiment, the left 1501 and right 1502 fingers are from different hands. The retractable multi-use cardiac monitor 110 as illustrated in FIG. 15 may collect ECG data from a patient when that patient applies the left 1501 and right 1502 side fingers onto the left 903 and right 904 sensing connectors, respectively. FIG. 16 is also an illustration of a finger electrode configuration of the retractable multi-use cardiac monitor 110 with the wire 501 retracted. The FIG. 16 embodiment illustrates a left 1501 and right 1502 finger attached to the left 903 and right 904 sensing connectors, respectively. In the illustrated embodiments of FIGS. 15 and 16, the left 903 and right 904 sensing connectors may be contacted to any body part of a patient to collect ECG data. For example, and without limitation, left 903 and right 904 sensing connectors may be contacted to the chest, the legs, ankles, wrists or the arms of a patient. Also for example, and without limitation, the left 903 and right 904 sensing connectors may be designed with different shapes or sizes. In some embodiments, the left 903 and right 904 sensing connectors may be shaped to receive a finger. As an example, a patient may not be feeling well, and may desire to make a short recording of ECG data without attaching wearable electrodes by merely holding the left 903 and right 904 sensing connectors against their chest for a short period. As a further example, a patient may desire to temporarily hold the left 903 and right 904 sensing connectors against his chest by moving the left 401 and right 402 sides of the retractable multi-use cardiac monitor 110 away from one another to create an optimum vector length as illustrated in FIG. 14A.

Figure 17:
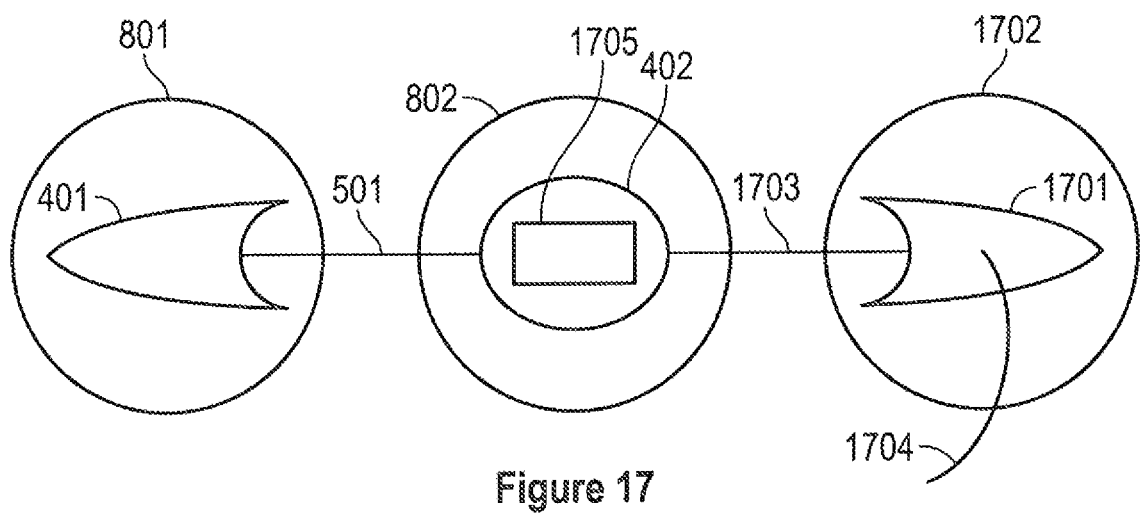
FIG. 17 is a top-down view of a retractable multi-use cardiac monitor that includes multiple additional wires, according to one embodiment.

FIG. 17 is a top-down view of a retractable multi-use cardiac monitor 110 that may include a second retractable wire 1703, according to another embodiment of the present invention. In the illustrated embodiment, the retractable multi-use cardiac monitor 110 may include a second wire 1703 that may be connected to a third portion 1701 of the retractable multi-use cardiac monitor 110. The third portion 1701 may also be attached to a third 1702 wearable electrode and may be comprised of a third housing (also referenced as 1701). The third wearable electrode 1702 may be connected to a patient's skin along with the left 801 and right 802 side wearable electrodes, thereby providing an increased number of electrode contacts on the patient's skin and increasing the quality of the collected ECG signal. In an alternative embodiment, the third wearable electrode 1702 may be used as a ground. In one embodiment, the second wire 1703 may retract into the right side 402. In an alternative embodiment, the second wire 1703 may retract into the third portion 1701. In one embodiment, the second wire 1703 may be detachable from the third portion 1701. In an alternative embodiment, the second wire 1703 simply may plug into a portion of the right side 402. In further embodiments, there may be an unlimited number of retractable or connectable wires which may retract or may connect to either the left 401 or right sides 402 for use in the collection of electrical signals from a patient's heart, for reference wires, or electrical grounds. For example, FIG. 17 also illustrates a simple wire 1704 that may be connected to the top of the right 402 side of the retractable multi-use cardiac monitor 110. Wire 1704 may be a ground or a signal wire.

FIG. 17 also illustrates a symptom button 1705. The symptom button 1705 may operate as described above with respect to FIG. 4. Additionally, the symptom button may be used when a patient desires to collect a short amount of data by temporarily placing the retractable multi-use cardiac monitor 110 against the patient's body, or if the patient desires to collect data using the sensing connectors 903 and 904 as finger electrodes as discussed in FIGS. 15 and 16. In such an embodiment, only two of the left 401 and right 402 sides or the third portion 1701 may be active for the collection of ECG data. In such an embodiment, the symptom button 1705, or a dip switch or other means, may be used to indicate to the monitor that only two of three electrodes will be used. For example, the symptom button 1705, or a dip switch or other means, may be used to disable the right 402 side, leaving only the left side 401 and the third portion 1701 active for the collection of ECG data during temporary placement of the retractable multi-use cardiac monitor 110 against a portion of a patient's body. The non-designation of the right side 402 during data collection may advantageously eliminate any electrical noise that may be provided by the right side 402 during collection and may allow for electrical isolation of the left side 401 and right portion 1701 relative to one another.

Figure 18:
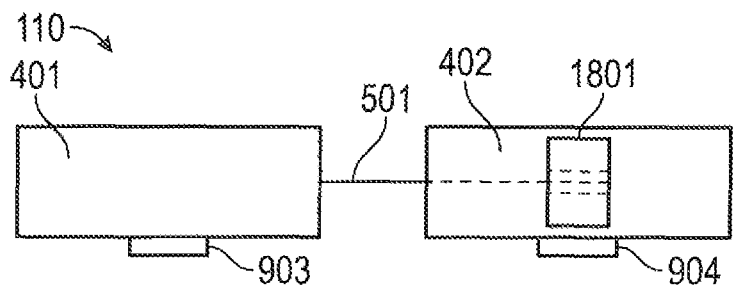
FIG. 18 is a side-view of a retractable multi-use cardiac monitor, according to one embodiment.
Figure 19:
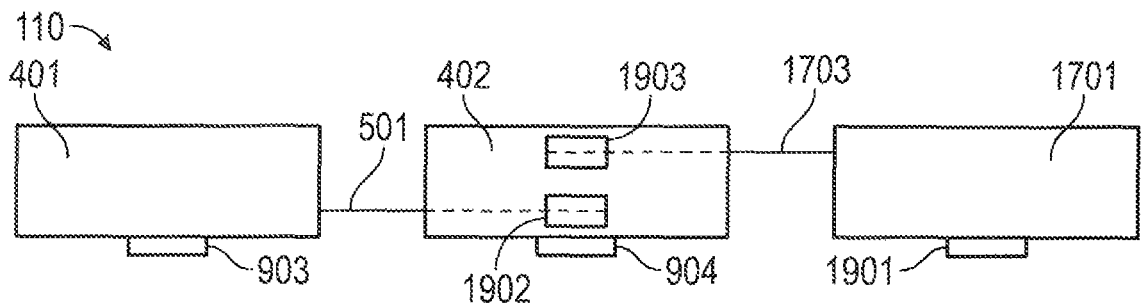
FIG. 19 is a side-view of a retractable multi-use cardiac monitor, according to one embodiment.
Figure 20:
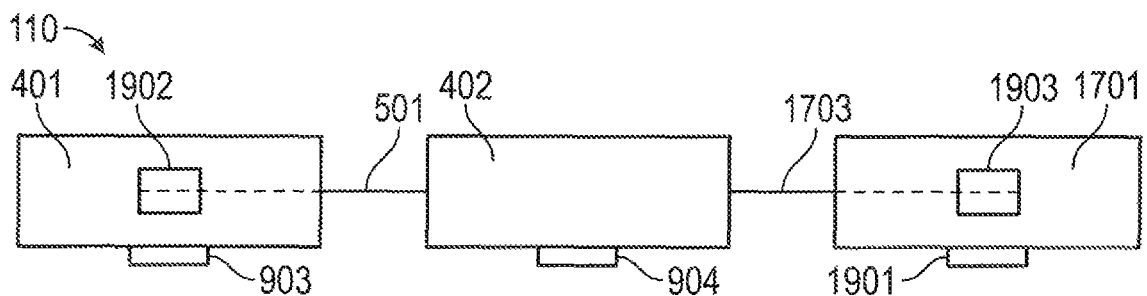
FIG. 20 is a side-vide of a retractable multi-use cardiac monitor, according to one embodiment.

FIG. 18 is a side-view of a retractable multi-use cardiac monitor, according to one embodiment of the present invention. FIG. 18 illustrates an embodiment where the wire 501 may retract into the right 402 side of the retractable multi-use cardiac monitor 110 using a single wire retraction barrel 1801 as a wire retractor. As discussed above, the wire 501 may retract into the left 401 side of the retractable multi-use cardiac monitor 110, and in such an embodiment the left 401 side may include a single wire retraction barrel as a wire retractor. FIG. 19 is also a side-view of a retractable multi-use cardiac monitor, according to one embodiment of the present invention. The embodiment illustrated in FIG. 19 includes left 401 and right 402 sides as well as a third portion 1701. The illustrated embodiment also includes a wire 501 and a second wire 1703. The wire 501 and second wire 1703 may retract into the right side 402 by a first 1902 and second 1903 retraction barrel, respectively, as wire retractors. The FIG. 19 embodiment also illustrates a third sensing connector 1901. FIG. 20 is a further illustration of a side-view of a retractable multi-use cardiac monitor 110, according to one embodiment of the present invention. In the FIG. 20 embodiment, the first retraction barrel 1902 may be within the left side 401 and the second retraction barrel 1903 may be within the third portion 1701. In the illustrated embodiment, the wire 501 may retract into the left side 401 by the first retraction barrel 1902, and the second wire 1703 may retract into the third portion 1701 by the second retraction barrel 1903.

Figure 21:
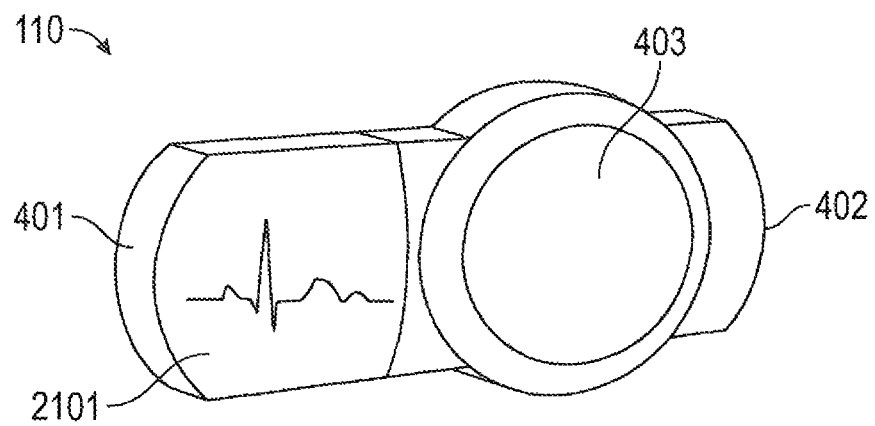
FIG. 21 is a top-down view of a retractable multi-use cardiac monitor, according to one embodiment.
Figure 22:
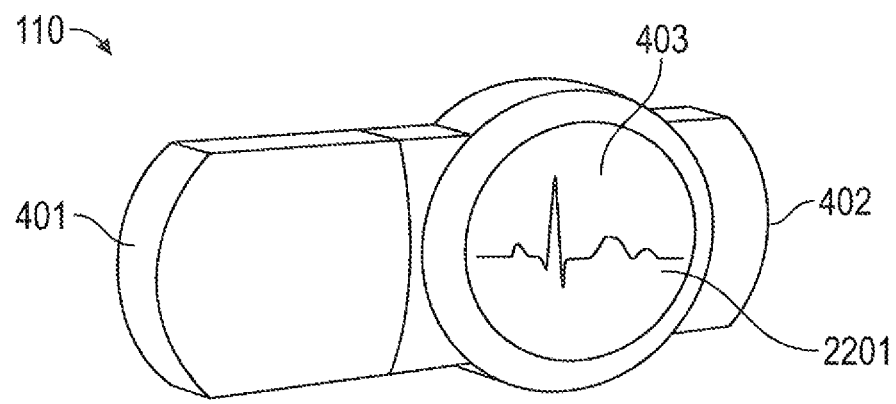
FIG. 22 is a top-down view of a retractable multi-use cardiac monitor, according to one embodiment.

FIG. 21 is yet another illustration of an embodiment of a retractable multi-use cardiac monitor 110. The illustrated embodiment includes left 401 and right 402 sides. The illustrated embodiment also includes a display screen 2101 which may be configured to display captured ECG or other biological data. FIG. 22 similarly illustrates an embodiment of a retractable multi-use cardiac monitor 110, where a display screen 2201 may be provided on the right side 402 in conjunction with the symptom button 403.

Figures 23A, 23B, 23C:
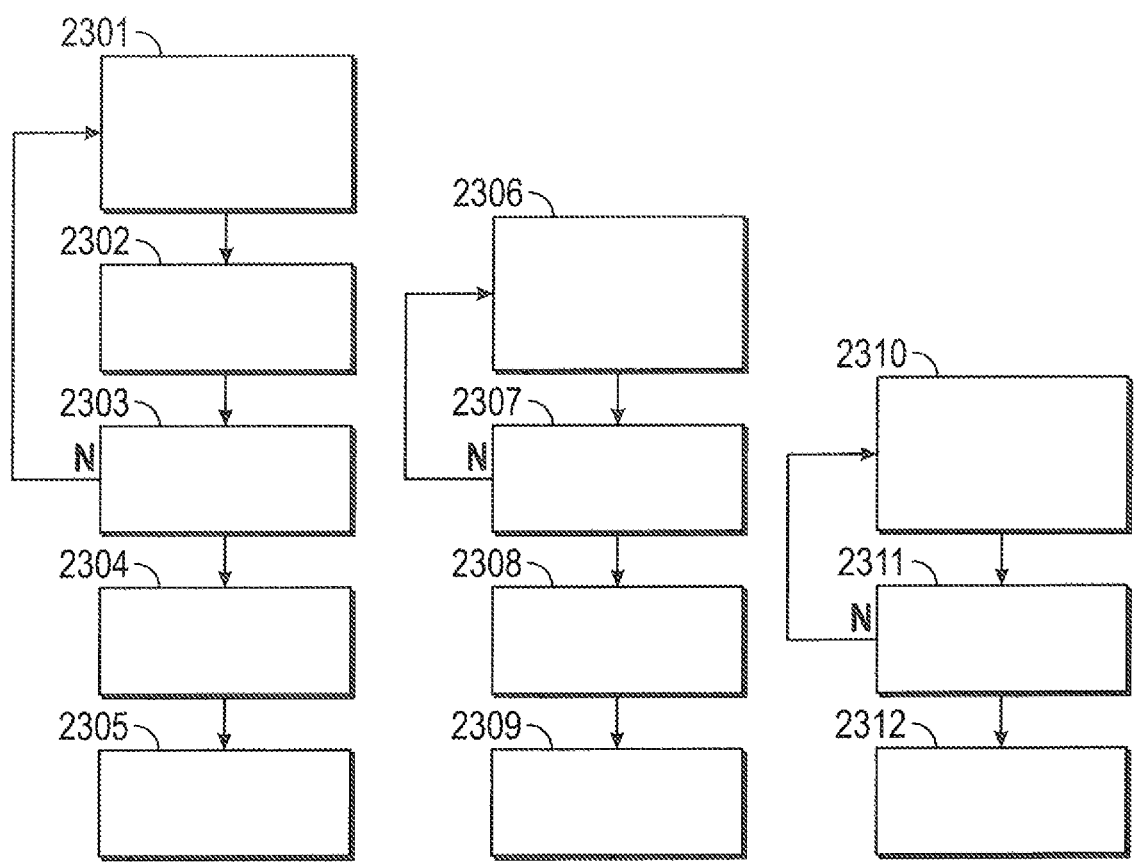
FIG. 23A is a flowchart illustrating the determination of a set of optimum electrode vector lengths, according to one embodiment.
FIG. 23B is a flowchart illustrating the determination of a set of optimum electrode vector lengths, according to one embodiment.
FIG. 23C is a flowchart illustrating the determination of a set of optimum electrode vector lengths, according to one embodiment.

FIG. 23A is a flowchart illustrating the determination of an optimum set of electrode vector lengths, according to one embodiment. The embodiment of FIG. 23A is directed to the determination of an optimum set of electrode vector lengths with an embodiment of the retractable multi-use cardiac monitor 110 that may include both left 401 and right sides 402, as well as a third portion 1701 as illustrated, for example, and without limitation, in FIGS. 17, 19, and 20 and discussed above. The FIG. 23A flowchart illustrates the steps of optimum electrode vector length determination from the perspective of a cardiac monitor (e.g. base unit 105 of FIG. 1 or smart phone of FIG. 3A), in an embodiment where a retractable multi-use cardiac monitor 110 may be used with another cardiac monitor to determine the optimum electrode vector length between the left 903 and right 904 sensing connectors, as well as the optimum electrode vector length between the right sensing connector 904 and the third sensing connector 1901. In step 2301, data may be received by the cardiac monitor (e.g. base unit 105 of FIG. 1 or smart phone of FIG. 3A) from the retractable multi-use cardiac monitor 110 representing a distance between the left 401 and right 402 sides of the retractable multi-use cardiac monitor 110 (and consequently left 903 and right 904 sensing connectors), as well as data representing a distance between the right side 402 and the third portion 1701 of the retractable multi-use cardiac monitor 110 (and consequently the right sensing connector 904 and the third sensing connector 1901). In some embodiments, if any of the left 401 side, right 402 side, or third portion 1701 have not moved since a previous iteration, a determination may be made by not sensing any such movement. In step 2302, ECG data collected by the retractable multi-use cardiac monitor 110 at the current distances between the left side 401, right side 402, and third portion 1701, respectively, may be received by the cardiac monitor (e.g. base unit 105 of FIG. 1 or smart phone of FIG. 3A). In step 2303, the received ECG collected data and the data representing the distance between the left 401 and right 402 sides, and the distance between the right side 402 and the third portion 1701 may be recorded by the cardiac monitor (e.g. base unit 105 of FIG. 1 or smart phone of FIG. 3A). The received ECG collected data and the data representing the distances between the left side 401, right side 402, and third portion 1701, respectively, may be recorded in a memory. Steps 2301 through 2303 may be repeated a number of times N with various distances between the left side 401, right side 402, and third portion 1701, respectively, of the retractable multi-use cardiac monitor 110. In some embodiments, the number of times N may be variable. In other embodiments, the number of times N may be constant. In yet other embodiments, the number of times N may be variable and may depend on intermediate calculations performed from the collected ECG data and distance values. In step 2304, a set of optimum electrode vector lengths between the left side 401, right side 402, and third portion 1701, respectively, may be calculated based on the ECG and distance data recorded in Step 2303 by the processor of the cardiac monitor (e.g. by the processor of base unit 105 of FIG. 1 or the processor of smart phone 301 of FIG. 3A). In step 2305, a notification may be generated indicating the optimum set of electrode vector lengths has been found. The notification may be generated by the cardiac monitor (e.g. base unit 105 of FIG. 1 or smart phone of FIG. 3A) or the retractable multi-use cardiac monitor 110. In some embodiments, the notification may be an audible noise. In other embodiments, the notification may be visual such as by a light or a display on a visual display (e.g. 2101 of FIG. 21 or 2201 of FIG. 22) of the retractable multi-use cardiac monitor 110, or by a light or a visual display on the display of a cardiac monitor (e.g. on a display 175 of base unit 105 of FIG. 1 or a display 305 of smart phone 301 of FIG. 3A).

In one embodiment, a set of optimum vector lengths may be calculated based on comparison of recorded signal strengths of ECG data at various vector distances collected by Steps 2301 through 2303. In another embodiment, a set of optimum vector lengths may be calculated based on comparison of recorded signal fidelities of ECG data at various vector distances collected by Steps 2301 through 2303. In another embodiment, a set of optimum vector lengths may be calculated based on comparison of both recorded signal strengths as well as recorded signal fidelities of ECG data at various vector distances collected by Steps 2301 through 2303. In yet other embodiments, a set of optimum vector lengths may be calculated based on analyzing the ECG data at various vector distances collected by Steps 2301 through 2303 to determine if the collected ECG data represents a high fidelity QRS ECG pattern. In yet other embodiments, other signal quality measures may be used to calculate an optimum vector length. The intermediate calculations noted above in reference to FIG. 23A may be any of these operations.

FIG. 23B is a flowchart illustrating the determination of an optimum set of electrode vector lengths, according to one embodiment of the present invention. The FIG. 23B flowchart illustrates the steps of optimum electrode vector length determination from the perspective of a retractable multi-use cardiac monitor 110 in an embodiment where the retractable multi-use cardiac monitor 110 may determine an optimum set of electrode vector lengths by itself. Further, the FIG. 23B flowchart is directed to the determination of an optimum set of electrode vector lengths in an embodiment of the retractable multi-use cardiac monitor 110 that may include both left 401 and right sides 402, as well as a third portion 1701 as illustrated, for example, in FIGS. 17, 19, and 20 and discussed above. In step 2306, the retractable multi-use cardiac monitor 110 may determine a distance between the left 401 and right 402 sides of the retractable multi-use cardiac monitor 110 (and consequently left 903 and right 904 sensing connectors), and distance between the right side 402 and the third portion 1701 of the retractable multi-use cardiac monitor 110 (and consequently the right sensing connector 904 and the third sensing connector 1901). In some embodiments, if any of the left 401, right 402, or third portion 1701 have not moved since a previous iteration, a determination may be made by not sensing any such movement. Data representing each of the distances may be recorded. In step 2307, the retractable multi-use cardiac monitor 110 may collect and may record ECG data using each of the left 903, right 904, and third 1901 sensing connectors. The ECG data collected and the distances between the left side 401, right side 402, and third portion 1701, respectively, may be recorded in a memory of the retractable multi-use cardiac monitor 110. Steps 2306 and 2307 may be repeated a number of times N with various distances between the left side 401, right side 402, and third portion 1701, respectively. In some embodiments, the number of times N may be variable. In other embodiments, the number of times N may be constant. In yet other embodiments, the number of times N may be variable and may depend on intermediate calculations performed from the collected ECG data and distances between the left side 401, right side 402, and third portion 1701, respectively. In step 2308, a set of optimum electrode vector lengths between the left side 401, right side 402, and third portion 1701, respectively, may be calculated based on the ECG and distance data collected in Steps 2306 and 2307 by a processor of the retractable multi-use cardiac monitor 110. In step 2309, a notification may be generated indicating the optimum set of electrode vector lengths has been found. In some embodiments, the notification may be an audible noise. In other embodiments, the notification may be visual such as by a light or a display on a display screen (e.g. 2101 of FIG. 21 or 2201 of FIG. 22) of the retractable multi-use cardiac monitor 110.

In one embodiment, a set of optimum vector lengths may be calculated based on comparison of recorded signal strengths of ECG data at various vector distances collected by Steps 2306 and 2307. In another embodiment, a set of optimum vector lengths may be calculated based on comparison of recorded signal fidelities of ECG data at various vector distances collected by Steps 2306 and 2307. In another embodiment, a set of optimum vector lengths may be calculated based on comparison of both recorded signal strengths as well as recorded signal fidelities of ECG data at various vector distances collected by Steps 2306 and 2307. In yet other embodiments, a set of optimum vector lengths may be calculated based on analyzing the ECG data at various vector distances collected by Steps 2306 and 2307 to determine if the collected ECG data represents a high fidelity QRS ECG pattern. In yet other embodiments, other signal quality measures may be used to calculate an optimum vector length. The intermediate calculations noted above in reference to FIG. 23B may be any of these operations.

FIG. 23C is a flowchart illustrating the determination of a set of optimum electrode vector lengths, according to one embodiment of the present invention. The FIG. 23C flowchart illustrates the steps of optimum electrode vector length determination from the perspective of a patient or a healthcare professional. In FIG. 23C, the retractable multi-use cardiac monitor 110 alone or in combination with another cardiac monitor may be configured to assist the patient or healthcare professional with the determination of a set of optimum electrode vector lengths as explained in FIGS. 23A and 23B above. The embodiment of FIG. 23C is directed to the determination of an optimum set of electrode vector lengths with an embodiment of the retractable multi-use cardiac monitor 110 that may include both left 401 and right sides 402, as well as a third portion 14071 as illustrated, for example, in FIGS. 17, 19, and 20 and discussed above. In step 2310, the patient or healthcare professional may adjust at least one of a distance between the left 401 and right 402 sides of the retractable multi-use cardiac monitor 110, or a distance between the right side 402 and the third portion 1701. In step 2310, the patient or healthcare professional may adjust both distances. In step 2311, the patient or healthcare professional may hold or may apply the retractable multi-use cardiac monitor 110 against a portion of a patient body to record data. Steps 2311 and 2312 may be repeated a number of times N with various distances between the left side 401, right side 402, and third portion 1701, respectively. In some embodiments, the number of times N may be variable. In other embodiments, the number of times N may be constant. In yet other embodiments, the number of times N may be variable and depends on intermediate calculations performed from the collected data and distance adjustments. In step 2312, the patient or healthcare professional may receive a notification indicating that the set of optimum electrode vector lengths has been found from either a cardiac monitor (e.g. base unit 105 of FIG. 1 or smart phone 301 of FIG. 3A) or from the retractable multi-use cardiac monitor 110, as explained above in the discussion of FIGS. 23A and 23B. In an alternative embodiment, the patient or healthcare professional may not receive a notification in step 2312. Rather, the patient or healthcare professional may review the iteratively collected ECG data at various vector distances to determine the set of optimum vector lengths. For example, the patient or healthcare professional may review such data on a display screen (e.g. 2101 of FIG. 21 or 2201 of FIG. 22) of the retractable multi-use cardiac monitor 110, on a display screen of a cardiac monitor (e.g. display 175 of base unit 105 of FIG. 1 or display 305 of smart phone 301 of FIG. 3A).

One of skill in the art would recognize that the methods of determining a set of optimum vector lengths as disclosed above in reference to FIGS. 23A, 23B, and 23C are similarly applicable to a retractable multi-use cardiac monitor 110 with any number of portions or sides that include sensing connectors or electrodes, or any number of wires that are connected to sensing connectors or electrodes.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated. Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Thus the scope of the invention should be determined by the appended claims and their legal equivalents, and not by the examples given.

That which is claimed is:

1. A retractable multi-use cardiac monitor, comprising:
   a memory;
   a first side comprising a first housing wherein a first sensing connector is on the outside of the first housing and is configured to collect electrocardiogram (ECG) data and store ECG data onto the memory;
   a second side comprising a second housing including a wire retractor and a second sensing connector, wherein the second sensing connector is on the outside of the second housing and is configured to collect ECG data and store ECG data, onto the memory, and wherein the wire retractor is configured to extend and retract a wire that connects the second and first sides to vary a linear distance between the second and first sensing connectors, defined as an interelectrode distance; and
   a processor that calculates
   an optimum electrode vector length between the first sensing connector and the second sensing connector based at least in part on the ECG data and on the interelectrode distance a data communication device providing data communication between the memory and the processor.

2. The retractable multi-use cardiac monitor according to claim 1, wherein the second side further comprises a symptom button on the outside of the second housing opposite the second sensing connector.

3. The retractable multi-use cardiac monitor according to claim 1, wherein the first and second sensing connectors are configured to connect to wearable electrodes.

4. The retractable multi-use cardiac monitor according to claim 1, wherein the first and second sensing connectors are shaped to receive a finger.

5. The retractable multi-use cardiac monitor according to claim 1, further comprising:
   a third portion comprising a third housing, wherein a third sensing connector is on the outside of the third housing and is configured to collect ECG data and store ECG data onto the memory; and
   a second wire that connects the third portion to the second side, wherein a second wire retractor of the second side is configured to extend and retract the second wire to vary a linear distance between the third and second sensing connectors, defined as a second interelectrode distance.

6. The retractable multi-use cardiac monitor according to claim 1 further comprising a wireless radio configured to transmit the interelectrode distance and a portion of collected ECG data from the memory to a destination.

7. The retractable multi-use cardiac monitor according to claim 6, wherein the destination is a smart phone.

8. The retractable multi-use cardiac monitor according to claim 6, wherein the wireless radio is configured to directly transmit to a monitoring center as the destination.

9. The retractable multi-use cardiac monitor according to claim 1, further comprising a display screen that is configured to display collected ECG data.

10. A method of collecting electrocardiogram (ECG) data with a retractable multi-use cardiac monitor, wherein the retractable multi-use cardiac monitor includes a processor and a memory, a first side that includes a first housing wherein a first sensing connector is on the outside of the first housing, a second side including a second housing including a wire retractor and a second sensing connector, wherein the second sensing connector is on the outside of the second housing, and a wireless radio, the method comprising:
   extending from the wire retractor a wire that connects the second and first sides to vary a linear distance between the second and first sensing connectors, defined as an interelectrode distance;
   collecting ECG data from the first and second sensing connectors of the retractable multi-use cardiac monitor, wherein the first and second sensing connectors are placed against the skin of a patient;
   recording the collected ECG data onto the memory of the retractable multi-use cardiac monitor;
   calculating, using the processor, an optimum electrode vector length between the first sensing connector and the second sensing connector based at least in part on the ECG data and on the interelectrode distance; and transmitting the interelectrode distance and a portion of the collected ECG data to a destination.

11. The method of collecting electrocardiogram (ECG) data according to claim 10, wherein the second side of the cardiac data monitor further comprises a symptom button on the outside of the second housing opposite the second sensing connector, the method further comprising:

receiving an indication that the symptom button of the retractable multi-use cardiac monitor has been pressed; and transmitting an indication that the symptom button of the retractable multi-use cardiac monitor has been pressed to the destination.

12. The method of collecting cardiac electrocardiogram (ECG) according to claim 10, wherein the first and second sensing connectors of the retractable multi-use cardiac monitor are configured to connect to wearable electrodes.

13. The method of collecting cardiac electrocardiogram (ECG) according to claim 10, wherein the first and second sensing connectors are shaped to receive a finger, and wherein the first sensing connector is placed against a first finger of a first hand of the patient and the second sensing connector is placed against a second finger of a second hand of the patient.

14. The method of collecting cardiac electrocardiogram (ECG) according to claim 10, wherein the retractable multi-use cardiac monitor further includes a third portion including a third housing, wherein a third sensing connector is on the outside of the third housing, the method further comprising:

extending from a second wire retractor of the second side a second wire that connects the third portion and second side to vary a linear distance between the third and second sensing connectors, defined as a second interelectrode distance; and collecting ECG data from the third sensing connector of the retractable multi-use cardiac monitor, wherein the third sensing connector is placed against the skin of the patient.

15. The method of collecting cardiac electrocardiogram (ECG) according to claim 10, wherein the transmitting step comprises transmitting the interelectrode distance and the portion of collected ECG data directly to at least one of a monitoring center and a smart phone as the destination.

16. The method of collecting cardiac electrocardiogram (ECG) according to claim 10, wherein the retractable multi-use cardiac monitor includes a display screen, the method further comprising:

displaying a portion of collected ECG data on the display screen.

17. A method of determining an optimum electrode vector length between a first sensing connector of a first side of a retractable multi-use cardiac monitor and a second sensing connector of a second side of the retractable multi-use cardiac monitor, comprising:

performing at least one data collection comprising the steps of:

determining a distance between the first sensing connector of the retractable multi-use cardiac data monitor and the second sensing connector of the retractable multi-use cardiac data monitor, wherein the distance defines an interelectrode distance, recording the interelectrode distance, collecting electrocardiogram (ECG) data through the first and second sensing connectors, and recording the collected ECG data;

calculating an optimum electrode vector length between the first sensing connector of the first side of the retractable multi-use cardiac monitor and the second sensing connector of the second side of the retractable multi-use cardiac monitor based on the ECG data recorded in the at least one data collection and the interelectrode distance recorded in the at least one data collection;

generating a notification of that the optimum electrode vector length has been found.

18. The method of determining the optimum electrode vector length according to claim 17 wherein the at least one data collection further comprises a plurality of data collections; wherein collecting ECG data further comprises recording an ECG signal strength collected by the first sensing connector and the second sensing connector as positioned at a respective distance during each of the plurality of data collections: and wherein calculating the optimum electrode vector length further comprises comparing the ECG signal strengths.

19. The method of determining the optimum electrode vector length according to claim 17 wherein the at least one data collection further comprises a plurality of data collections; wherein collecting ECG data further comprises recording an ECG fidelity collected by the first sensing connector and the second sensing connector as positioned at a respective distance during each of the plurality of data collections; and wherein calculating the optimum electrode vector length further comprises comparing the ECG fidelities.

20. The method of determining the optimum electrode vector length according to claim 17 wherein calculating the optimum electrode vector length further comprises:

determining that the ECG data represents a high fidelity QRS ECG pattern, and setting the optimum electrode vector length to equal the interlectrode length.

* * * * *